(12) United States Patent
Sheikh et al.

(10) Patent No.: US 12,186,369 B2
(45) Date of Patent: Jan. 7, 2025

(54) GENE THERAPY STRATEGY TO RESTORE ELECTRICAL AND CARDIAC FUNCTION, AND CARDIAC STRUCTURE, IN ARRHYTHMOGENIC RIGHT VENTRICULAR CARDIOMYOPATHY

(71) Applicant: THE REGENTS OF THE UNIVERSITY OF CALIFORNIA, Oakland, CA (US)

(72) Inventors: Farah Sheikh, La Jolla, CA (US); Jing Zhang, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 518 days.

(21) Appl. No.: 16/648,922

(22) PCT Filed: Sep. 20, 2018

(86) PCT No.: PCT/US2018/052057
§ 371 (c)(1),
(2) Date: Mar. 19, 2020

(87) PCT Pub. No.: WO2019/060619
PCT Pub. Date: Mar. 28, 2019

(65) Prior Publication Data
US 2020/0215155 A1 Jul. 9, 2020

Related U.S. Application Data

(60) Provisional application No. 62/560,989, filed on Sep. 20, 2017.

(51) Int. Cl.
*C12N 15/00* (2006.01)
*A61K 35/761* (2015.01)
(Continued)

(52) U.S. Cl.
CPC .......... *A61K 38/177* (2013.01); *A61K 35/761* (2013.01); *A61P 9/06* (2018.01);
(Continued)

(58) Field of Classification Search
None
See application file for complete search history.

(56) References Cited

U.S. PATENT DOCUMENTS 6,309,634 B1 10/2001 Bankiewicz et al.
7,317,950 B2 1/2008 Lee
(Continued)

FOREIGN PATENT DOCUMENTS

CN 1703257 A 11/2005
CN 106596972 A 4/2017
(Continued)

OTHER PUBLICATIONS

Lyon et al., "Connexin defects underlie arrhythmogenic right ventricular cardiomyopathy in a novel mouse model," Human Molecular Genetics, vol. 23, No. 5: 1134-1150 (Year: 2014).*
(Continued)

*Primary Examiner* — M Franco G Salvoza
(74) *Attorney, Agent, or Firm* — Perkins Coie LLP

(57) ABSTRACT

Disclosed herein are methods of treating arrhythmogenic right ventricular cardiomyopathy in a subject, comprising administering a gene therapy construct comprising a connexin 43 sequence, wherein as a result of the administration, connexin 43 levels in at least a portion of the heart are increased. Further disclosed are other cardiovascular diseases can be treated with the method.

12 Claims, 11 Drawing Sheets

Specification includes a Sequence Listing.

(51) Int. Cl.
    *A61K 38/17*     (2006.01)
    *A61P 9/06*     (2006.01)
    *C12N 7/00*     (2006.01)
    *C12N 15/86*     (2006.01)
    *A61K 48/00*     (2006.01)

(52) U.S. Cl.
    CPC .............. *C12N 7/00* (2013.01); *C12N 15/86* (2013.01); *A61K 48/00* (2013.01); *C12N 2710/10343* (2013.01); *C12N 2750/14143* (2013.01)

(56) References Cited

U.S. PATENT DOCUMENTS

| | | |
|---|---|---|
| 7,494,644 B2 | 2/2009 | Lee |
| 7,840,263 B2 | 11/2010 | Girouard et al. |
| 10,501,756 B2 | 12/2019 | Hamburg-Eppendorf et al. |
| 2005/0260623 A1 | 11/2005 | Trosko et al. |
| 2006/0088503 A1 | 4/2006 | Sharma et al. |
| 2008/0019953 A1 | 1/2008 | Lee |
| 2009/0054828 A1 | 2/2009 | Stolen et al. |
| 2010/0179609 A1 | 7/2010 | Girouard et al. |
| 2011/0077702 A1* | 3/2011 | Boink ...................... A61N 1/00 607/9 |
| 2011/0129449 A1 | 6/2011 | Cohen et al. |
| 2011/0256112 A2* | 10/2011 | Cohen ...................... A61P 9/00 435/325 |

FOREIGN PATENT DOCUMENTS

| | | | |
|---|---|---|---|
| JP | 2005527482 A | 9/2005 | |
| JP | 2008506467 A | 3/2008 | |
| JP | 2008515997 A | 5/2008 | |
| WO | 1998/8002150 A1 | 1/1998 | |
| WO | 2002/019966 A2 | 3/2002 | |
| WO | 2003/039344 A2 | 5/2003 | |
| WO | 2006/019856 A1 | 2/2006 | |
| WO | 2006/044589 A2 | 4/2006 | |
| WO | WO-2006134494 A2 * | 12/2006 | ............. A61K 31/70 |
| WO | 2009/025812 A2 | 2/2009 | |
| WO | 2017/152149 A1 | 9/2017 | |
| WO | 2017/180896 A1 | 10/2017 | |
| WO | 2021/025725 A1 | 2/2021 | |

OTHER PUBLICATIONS

Fishman et al., "The Human Connexin Gene Family of Gap Junction Proteins: Distinct Chromosomal Locations but Similar Structures," Genomics 10: 250-256 (Year: 1991).*
Bikou et al. "Connexin 43 gene therapy prevents persistent atrial fibrillation in a porcine model," Cardiovasc Res 92:218-225, 2011.
Fernandes et al. "Cardiac cell therapy: overexpression of connexin43 in skeletal myoblasts and prevention of ventricular arrhythmias," J Cell Mol Med 13:3703-3712, 2009.
Fidler et al. "Abnormal connexin43 in arrhythmogenic right ventricular cardiomyopathy caused by plakophillin-2 mutations," J Cell Mol Med 13:4219-4228, 2009.
Kurotobi et al. Multiple arrhythmogenic foci associated with the development of perpetuation of atrial fibrillation. Circ Arrhythm Electrophysiol 3:39-45, 2010.
Wolfram and Donohue "Gene therapy to treat cardiovascular disease," J Am Heart Assoc 2013;2:e000119 doi: 10.1161/JAHA.113.000119.
Chelko et al. "Central role for GSK3b in the pathogenesis of arrhythmogenic cardiomyopathy," JCI Insight. 2016; 1(5):e85923. doi:10.1172/jci.insight.85923.
Lyon et al. "Connexin defects underlie arrhythmogenic right ventricular cardiomyopathy in a novel mouse model," Hum Mol Genet 23:1134-1150, 2014.
Greener et al. "Connexin43 gene transfer reduces ventricular tachycardia susceptibility after myocardial infarction," 60:1103-1110, 2012.
Garashi et al. "Connexin gene transfer preserves conduction velocity and prevents atrial fibrillation," Circulation 125:216-225, 2012.
Asokan and Samulski "An Emerging Adeno-Associated Viral Vector Pipeline for Cardiac Gene Therapy," Hum Gene Ther. 24(11): 906-913, 2013.
Phillips et al. "Systemic Gene Transfer to Skeletal Muscle Using Reengineered AAV Vectors," Methods Mol Biol. 709:141-51, 2011.
Pacak and Byrne "AAV Vectors for Cardiac Gene Transfer: Experimental Tools and Clinical Opportunities," Mol. Ther. 19(9):1582-1590, 2011.
Ozawa "Gene Therapy Using AAV Vectors," Drug Delivery System, 2007, vol. 22-6, pp. 643-650.
"Arrhythmogenic right ventricular cardiomyopathy," Jpn. J. Electrocardiology, 2014, vol. 43, No. 3, pp. 245-263.
Wu and Lu "Loss of anti-arrhythmic effect of vagal nerve stimulation on ischemia-induced ventricular tachyarrhythmia in aged rats," Tohoku Journal of Experimental Medicine, 2011, vol. 223, No. 1, pp. 27-33.
Chinese Office Action dated Aug. 22, 2023 for Chinese Application No. 201880061433.4, 6 pages (with unofficial translation).
Chen, Guiying et al., MG132 proteasome inhibitor upregulates the expression of connexin 43 in rats with adriamycin-induced heart failure, Molecular Medicine Reports 12: 7595-7602 (Year: 2015).
JPO, Notice of Decision to Grant dated Nov. 28, 2023 for Application No. 2020-516572, 3 pages.
Israel Patent Office, First Office Action dated Nov. 12, 2023 for Application No. 273448, 4 pages.
USPTO, Non-Final Office Action dated Mar. 30, 2023 for U.S. Appl. No. 16/862,326, 18 pages.
USPTO, Notice of Allowance dated Jan. 4, 2024 for U.S. Appl. No. 16/862,326, 12 pages.
Zhang et al., "Silencing of desmoplakin decreases connexin43/ Nav1.5 expression and sodium current in HL-1 cardiomyocytes," Molecular Medicine Reports 8: 780-786 (Year: 2013).
USPTO, Notice of Allowance for U.S. Appl. No. 16/862,326, mailed on Apr. 10, 2024, 8 pages.
EPO, Extended European Search Report for Application No. 23210043.8, mailed May 13, 2024, 8 pages.
Asokan et al., "Reengineering a receptor footprint of adeno-associated virus enables selective and system gene transfer to muscle," Nat Biotechnol. (1):79-82, 2010.
EPO, Extended European Search Report for Application No. 188858620.0, Mail Date: May 25, 2021, 7 pages.
IP Office China, First Office Action with Search Report for Application No. 201880061433.4, Mail Date: May 25, 2021.
IP Office China, Second Office Action with Search Report for Application No. 201880061433.4, Mail Date: Mar. 10, 2023.
IP Office Japan, Notice of Reasons for Refusal for Application No. 2020-516572, Mail Date: Jul. 26, 2022.
IP Office Japan, Notice of Reasons for Refusal for Application No. 2020-516572, Mail Date: Mar. 7, 2023.
ISA/US, International Search Report and Written Opinion for Application No. PCT/US18/52057, Mail Date: Feb. 14, 2019, 14 pages.
Rickelt, "Plakophilin-2: a cell-cell adhesion plaque molecule of selective and fundamental importance in cardiac functions and tumor cell growth," Cell Tissue Res 348:281-294 (Year: 2012).
Smyth et al., "Autoregulation of connexin43 gap junction formation by internally translated isoforms," Cell Rep. 5(3):611-8, 2013.
USPTO, Notice of Allowance for U.S. Appl. No. 16/862,326, mailed on Jul. 26, 2024, 13 pages.
IP Office Australia, Exam Report No. 1 for Australian Application No. 2018335401, Mail Date: Jul. 31, 2024, 5 pages.
CIPO, Examiner's Report for Application No. 3,076,227, mailed Sep. 19, 2024, 2024, 5 pages.

* cited by examiner

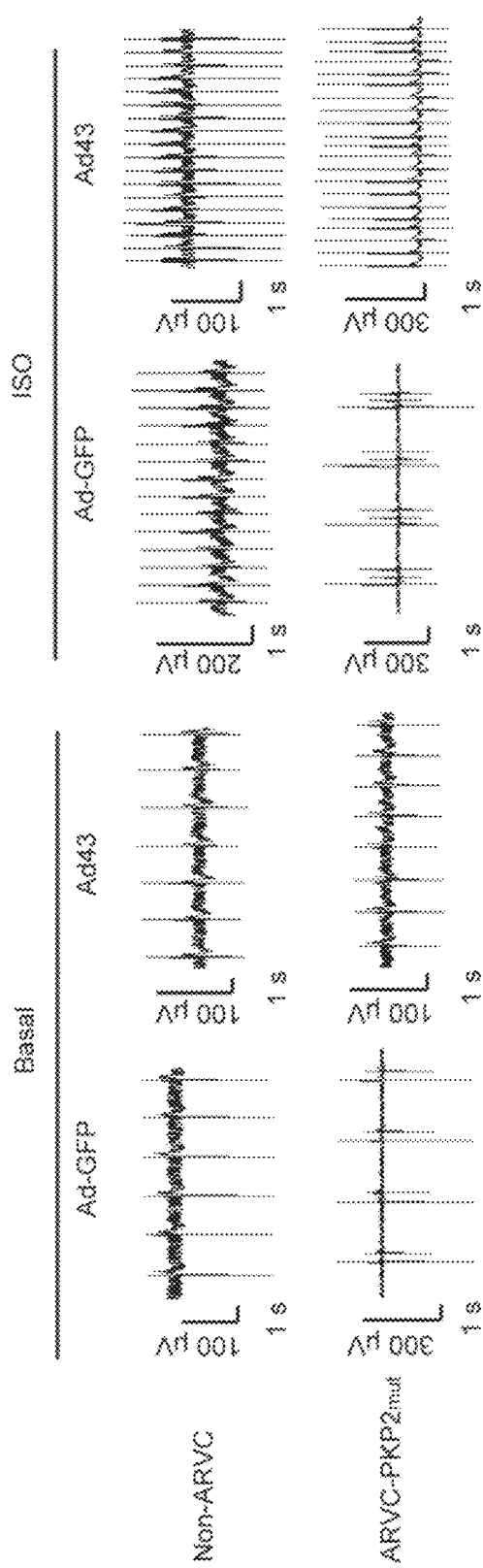
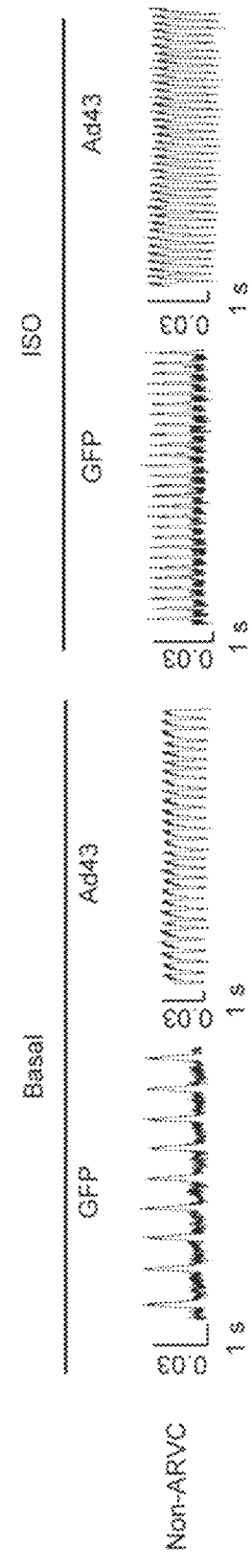
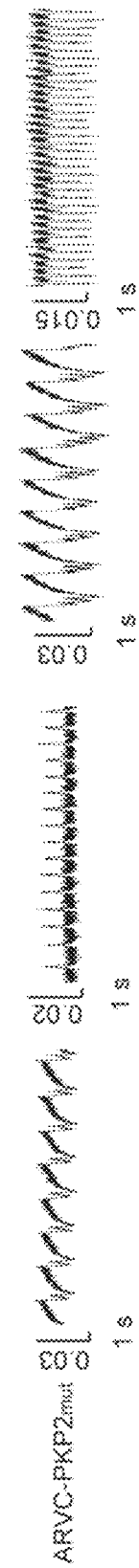
FIG. 1A
FIG. 1B
FIG. 1C
FIG. 1D

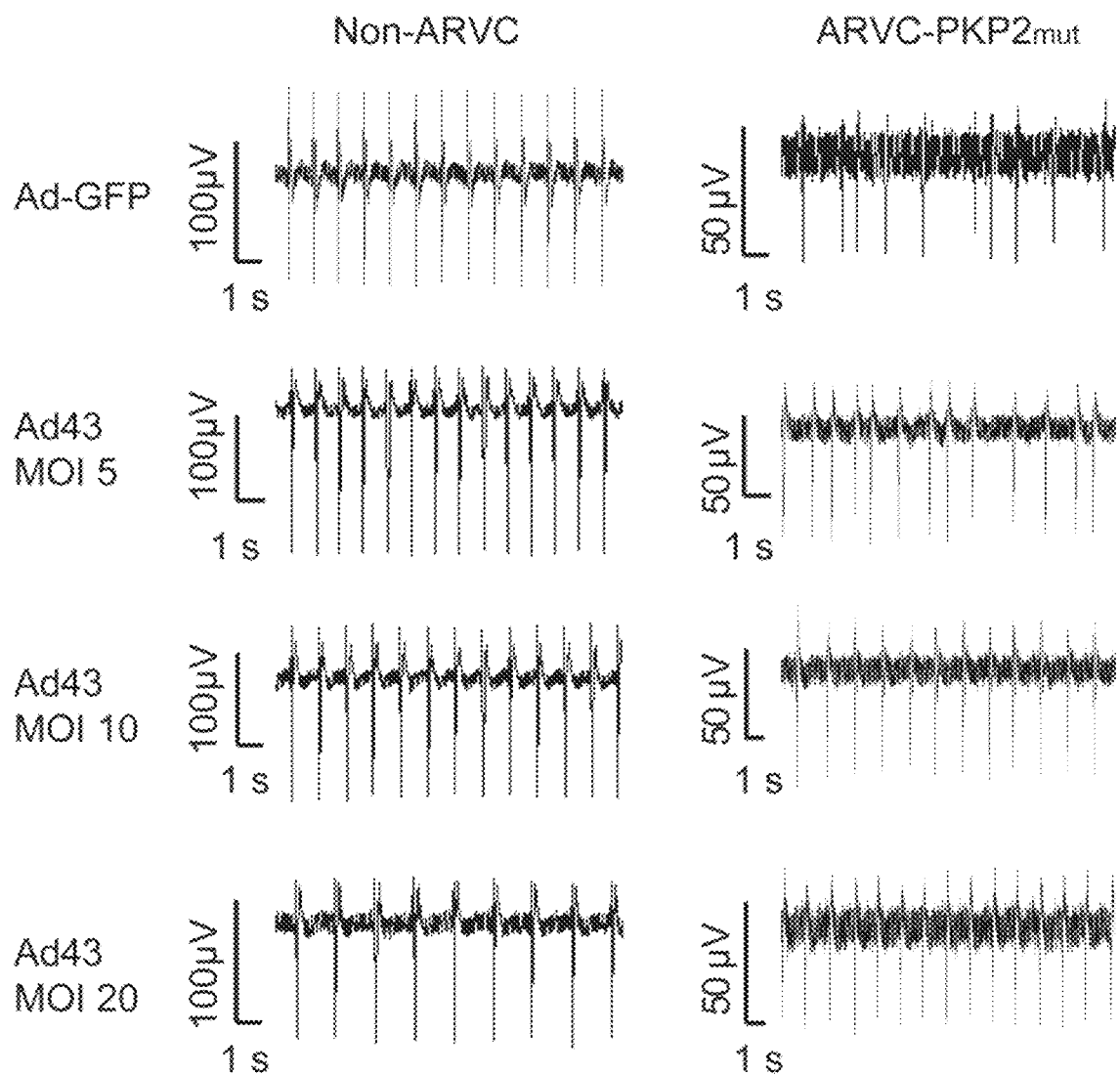

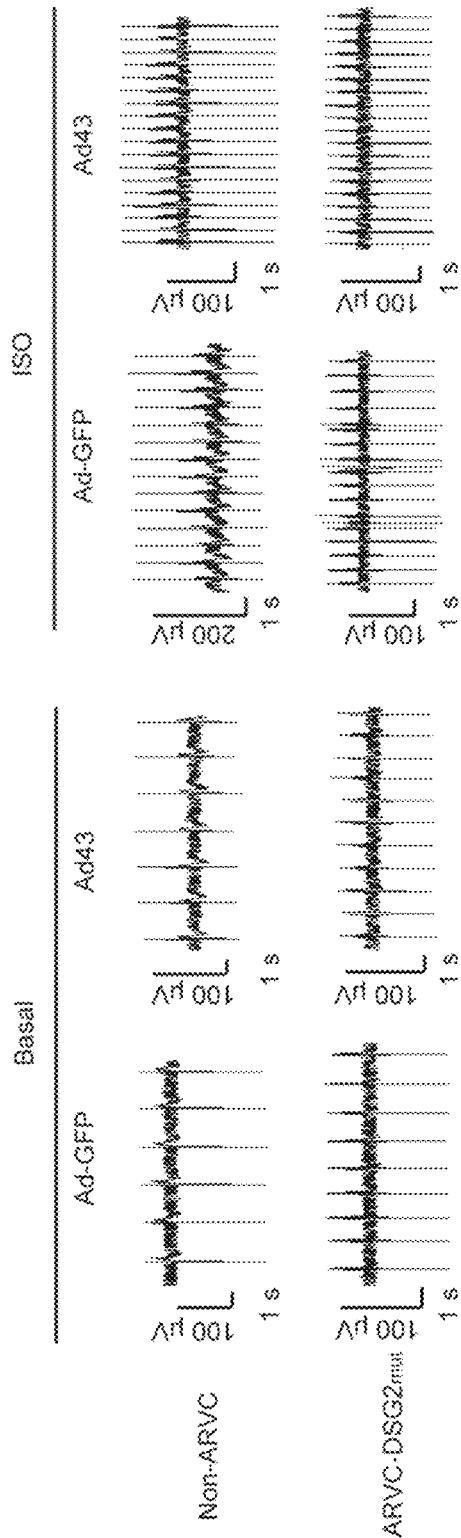
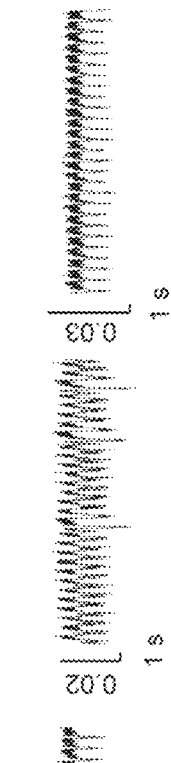
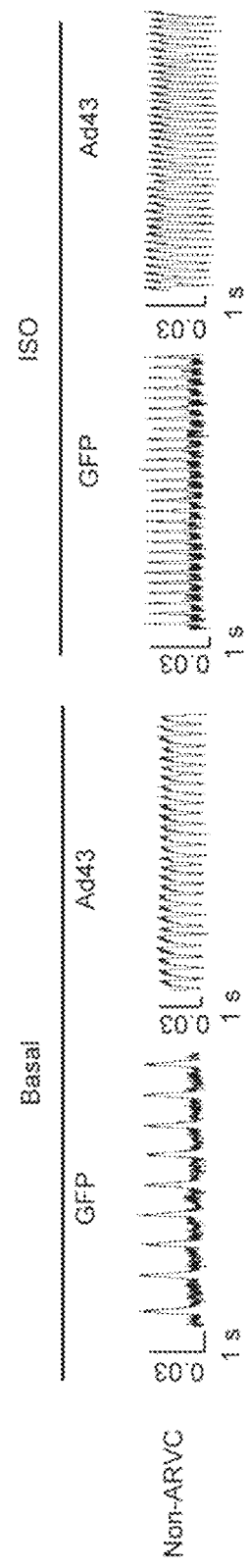
FIG. 3A
FIG. 3B
FIG. 3C
FIG. 3D

GENE THERAPY STRATEGY TO RESTORE ELECTRICAL AND CARDIAC FUNCTION, AND CARDIAC STRUCTURE, IN ARRHYTHMOGENIC RIGHT VENTRICULAR CARDIOMYOPATHY

CROSS-REFERENCE TO RELATED APPLICATIONS

This application is a 35 U.S.C. 371 national phase entry of PCT/US2018/052057, filed Sep. 20, 2018, which claims the benefit under 35 U.S.C. 119(e) of U.S. Provisional Application 62/560,989 filed Sep. 20, 2017, the entire contents of which are each incorporated by reference herein.

GOVERNMENT SUPPORT

The present subject matter was made with government support under Grant Number HL095780-01 awarded by the National Institutes of Health. The Government has certain rights in the subject matter.

BACKGROUND

Arrhythmogenic right ventricular cardiomyopathy (ARVC) is a complex and devastating genetic based heart disease found in young individuals and athletes, which exhibits wide variability with respect to its clinical features. Classic ARVC clinical symptoms include palpitations, arrhythmic (pre)syncope and sudden cardiac death due to ventricular arrhythmias, and thus, characteristic of primary electrical involvement. However, ARVC patients also exhibit clinical symptoms associated with structural disease, which include myocardial remodeling consisting of thinning and dilation as well as functional deficits of the ventricles (right and/or left) and/or fibro-fatty replacement of the myocardium and thus, characteristic of primary structural involvement. The structural nature of the disease is further reinforced as ARVC is termed a "disease of the desmosome", as human genetic studies show that 40% of patients carry mutations in genes encoding components of the desmosomal cell-cell junction (e.g., desmoplakin (DSP), plakoglobin (JUP) plakophillin 2 (PKP2) and desmoglein 2 (DSG2)), which are crucial in maintaining the mechanical/structural integrity of cardiac cell junctions.

At present there are no effective treatments for ARVC as well as there have been no randomized trials of treatment modalities, screening regimens, or medications specific for ARVC. As a result, treatment strategies for ARVC patients are directed at symptomatic relief of primarily the electrophysiological defects, based on clinical expertise, results of retrospective registry-based studies, and the results of studies on model systems. As a result, existing therapies for ARVC patients rely upon use of anti-arrhythmic drugs (sotalol, amniodarone and beta-blockers) that transition into more invasive actions, which include implantable cardioverter defibrillators and cardiac catheter ablation, if the patient becomes unresponsive or intolerant to anti-arrhythmic therapies. However, current therapeutic modalities have limited effectiveness in managing the disease as 40% of ARVC patients (young disease) die within 10-11 years after initial diagnosis, highlighting the need for development of more effective therapies (and especially those that target the underlying structural nature of the disease) for patients with ARVC.

SUMMARY

Disclosed herein are methods of treating arrhythmogenic right ventricular cardiomyopathy in a subject, comprising, or alternatively consisting essentially of, or yet further consisting of, administering an effective amount of a gene therapy construct or vector comprising a connexin 43 polynucleotide sequence, wherein as a result of the administration, connexin 43 levels in at least a portion of the heart are increased. In some embodiments, the construct is an adenovirus construct. In some embodiments the construct is an adeno-associated virus construct.

Further embodiments include a construct or vector capable of conferring expression of connexin 43 on cardiac tissue. In some embodiments, the construct or vector is a plasmid or a viral vector, such as an adenovirus construct. In some embodiments the construct or vector is or an adeno-associated virus construct.

In some embodiments the connexin 43 polypeptide sequence is the 382 amino acid sequence of P17302 (CXA_1HUMAN; UniProtKB) (SEQ ID NO: 1). The encoding polynucleotide may have a polynucleotide sequence associated with P17302 or any other nucleic acid sequence encoding the same polypeptide sequence. In some embodiments the encoding nucleic acid sequence is GenBank CR541660.1 (SEQ ID NO: 2).

In some embodiments, as a result of the administration, cardiac electrical and structural dysfunction is reduced and structural integrity is improved. In some embodiments, as a result of the administration, cardiac physiologic dysfunction is reduced. In some embodiments, as a result of the administration, survival is prolonged.

BRIEF DESCRIPTION OF THE DRAWINGS

FIGS. 1A-1G depict that restoration of connexin 43 protein levels closer to wild type levels can rescue physiological abnormalities in ARVC-plakophilin-2 mutant ($PKP2_{mut}$) hiPSC-derived cardiomyocytes FIGS. 1A-1B depict representative field potential traces (note frequency and pattern of spikes in the trace) for Non-ARVC and ARVC-$PKP2_{mut}$ (also known as ARVC-Structural (S)) hiPSC-derived cardiomyocytes at basal level (FIG. 1A) and under isoproterenol (ISO) stimulation (FIG. 1B), which mimics conditions associated with stress/exercise, and that have been infected for 48 hours (h) with an adenovirus harboring green fluorescent protein (Ad-GFP) or adenovirus harboring connexin 43 (Ad43). Scale bar, vertical: amplitude of field potential (µV); horizontal: time (1 s). FIGS. 1C-1D depict representative impedance (contractility) trace (note frequency and shape of spikes in the trace) for Non-ARVC and ARVC-PKP2mut (ARVC-S) hiPSC-derived cardiomyocytes at basal level (FIG. 1C) and under ISO stimulation (FIG. 1D), with Ad-GFP or Ad43 infection for 48 h. Scale bar, vertical: cell index; horizontal: time (1 s). FIG. 1E depicts quantification of firing irregularity index at basal level of Non-ARVC and ARVC-$PKP2_{mut}$ iPSC-derived cardiomyocytes with Ad-GFP or Ad43 infection. Mean values with standard error of mean (s.e.m.), , p<0.01, n=6 (Non-ARVC), n=7 (ARVC-$PKP2_{mut}$), two sample t-test. FIG. 1F depicts quantification of firing irregularity index under ISO stimulus of Non-ARVC and ARVC-$PKP2_{mut}$ (ARVC-S) with Ad-GFP or Ad43 infection. Mean values with s.e.m, *, p<0.001, n=6 (Non-ARVC), n=7 (ARVC-$PKP2_{mut}$), two sample t test. FIG. 1G depicts expression levels of connexin 43 (Cx43), desmoplakin (DSP), desmoglein-2 (DSG2), plakoglobin (JUP) and plakophilin-2 (PKP2) in non-ARVC, ARVC-$PKP2_{mut}$(ARVC-S) and ARVC-desmoglein-2 mutant ($DSG2_{mut}$ (ARVC-E, also known as ARVC-Electrical (E)) hiPSC-derived cardiomyocytes with Ad-GFP or Ad43 infection for 48 h., a-myosin heavy chain (α-MHC), cardiomyocytes loading control, glyceraldehyde 3-phosphate dehydrogenase (GAPDH), loading control.

FIGS. 2A-2B depict that physiological abnormalities in ARVC-S cardiomyocytes can be rescued by Cx43 overexpression in a dose-dependent manner. Representative field potential traces from Non-ARVC (FIG. 2A) and ARVC-PKP2$_{mut}$ (FIG. 2B) hiPSC-derived cardiomyocytes after dose-dependent Ad43 infection are shown. Note that the irregular frequency and pattern of spikes in ARVC-PKP2$_{mut}$ hiPSC-derived cardiomyocytes becomes progressively more regular in frequency of spikes with increasing doses (MOI 5, MOI 10 and MOI 20) of Cx43. Scale bar, vertical: amplitude of field potential (pV); horizontal: time (1 s). MOI: multiplicity of infection.

FIGS. 3A-3F depict that restoration of connexin 43 protein levels can rescue physiological abnormalities in ARVC-DSG2$_{mut}$ (ARVC-E) hiPSC-derived cardiomyocytes under catecholamine (ISO) stimulation, to mimic exercise/stress conditions. FIGS. 3A-3B depict representative field potential trace for Non-ARVC and ARVC-DSG2$_{mut}$ hiPSC-derived cardiomyocytes at basal level (FIG. 3A) and under ISO stimulation (FIG. 3B) with Ad-GFP or Ad43 infection for 48 h. Scale bar, vertical: amplitude of field potential (pV); horizontal: time (1 s). FIGS. 3C-3D depict representative impedance (contractility) trace for Non-ARVC and ARVC-DSG2$_{mut}$ hiPSC-derived cardiomyocytes at basal level (FIG. 3C) and under ISO stimulation (FIG. 3D) with Ad-GFP or Ad43 infection for 48 h. Scale bar, vertical: cell index; horizontal: time (1 s). FIG. 3E depicts quantification of firing irregularity index at basal in Non-ARVC and ARVC-DSG2$_{mut}$ hiPSC-derived cardiomyocytes with Ad-GFP or Ad43 infection. Mean values with s.e.m., n=6 (Non-ARVC), n=6 (ARVC-DSG2$_{mut}$), two sample t-test. FIG. 3F depicts quantification of firing irregularity index under ISO stimulus of Non-ARVC and ARVC-DSG2$_{mut}$ (ARVC-E) with Ad-GFP or Ad43 infection. Mean values with s.e.m, *, p<0.05, n=6 (Non-ARVC), n=6 (ARVC-DSG2$_{mut}$), two sample t-test. Note the irregular frequency and pattern of spikes in ARVC-DSG2$_{mut}$ hiPSC-derived cardiomyocytes is only observed in ISO conditions and that restoration of Cx43 can make frequency and pattern of spikes more regular.

FIG. 4A depicts the experimental strategy for adeno-associated virus tagged with green fluorescent protein (AAV-GFP)/adeno-associated virus harboring connexin-43 and tagged with GFP (AAV-Cx43) injection and electrophysiological and cardiac function analysis. FIG. 4B depicts echocardiography of control and DSP-cKO mice (DSP floxed mice; Cre positive) at 6 weeks of age and prior to adeno-associated virus (AAV) injection, showed a significant decrease in fractional shortening (% FS) in DSP-cKO mice compared to control (DSP floxed mice; Cre negative). FIG. 4C depicts echocardiography of control and DSP-cKO mouse at four (10 weeks old) and five (11 weeks old)-weeks post-AAV injection, revealed an improvement in % FS (6% to 15%) in DSP-cKO mouse injected with AAV-Cx43. No significant changes in % FS could be observed in control mice injected with AAV-Cx43. No significant difference in heart rate was found between control and DSP-cKO mouse groups. FIG. 4D depicts representative surface ECG traces from control and DSP-cKO mouse at four (10 weeks old) and five (11 weeks old)-weeks post-AAV-Cx43 injection. DSP-cKO mouse showed severe arrhythmias (premature ventricular contractions (PVCs=extra beats that don't fall in line within regular pattern), series of QRS complex inversions (spikes pointing downward instead of upwards) indicative of bundle branch blocks) at four weeks post-AAV-Cx43 injection. However, at five weeks post-AAV-Cx43 injection, DSP-cKO show improvement in cardiac rhythm (1.5 fold less PVCs, limited QRS complex inversions (series of 10 in previous week (10 week) and only two in the following week (11 week)) as well as the appearance of normal sinus rhythm (regular frequency and rhythmic beats)). FIG. 4E depicts quantification of PVCs in DSP-cKO mouse at four (10 weeks old) and five (11 weeks old) weeks post-AAV-Cx43 injection revealed a 1.5 fold reduction in the number of PVCs at five weeks-post AAV-Cx43. FIGS. 4F-4H depicts survival (FIG. 4H), western blot analysis (FIG. 4F), and immunostaining analysis of GFP. (FIG. 4G) revealed restoration of Cx43 protein in a DSP-cKO mouse at five weeks post-AAV-Cx43 injection that survived (DSP-cKO2-AAV-Cx43, green). In contrast, no restoration of Cx43 protein was observed at three weeks post-AAV-Cx43 injection in a DSP-cKO mouse that died (DSP-cKO1-AAV-Cx43, red)

DETAILED DESCRIPTION

Figure 1E:
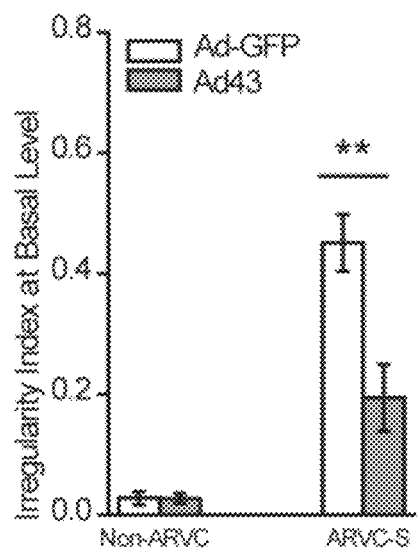
Figure 1F:
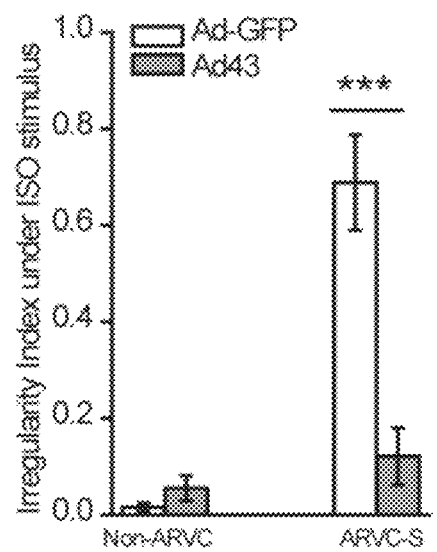

Disclosed herein is a gene therapy strategy to prolong life and rescue/treat cardiac electrical and structural dysfunction in the arrhythmogenic disorder, arrhythmogenic right ventricular cardiomyopathy via targeted restoration of connexin 43 in cardiac muscle cells using adeno-(associated) viral strategies. Although connexin 43 is known to impact electrical function in the heart, we show that connexin 43 restoration can also prolong life as well as improve contractile (structural) function in a genetic mouse model harboring a severe structural form of ARVC in late stages of disease (life). Studies in an in vitro human ARVC stem cell based model that exhibited severe structural deficits (as evidenced by destroyed desmosomal junctions via transmission electron microscopy assays) also revealed that connexin 43 restoration was sufficient to restore the electrical and contractile (structural) functional deficits in these diseased cells. Moreover, this restoration occurred rapidly. Since ARVC is a rare and fatal disease with no treatment, this approach represents the first opportunity to test treatment approaches in this very vulnerable population, and this strategy may also have applications to other cardiac diseases that have underlying structural defects associated with connexin 43 loss.

Human induced pluripotent stem cells (hiPSC) have shown tremendous potential for in vitro disease modeling of genetic based-cardiac diseases. Toward this end, the inventors of the present disclosure generated a panel of integration-free hiPSC lines from genetically, biochemically, and physiologically characterized patients afflicted by arrhythmogenic right ventricular cardiomyopathy (ARVC), a cardiac disease of the desmosomal cell-cell junction, known to manifest across a spectrum of symptomatic severities and cause sudden death in young people. Through ultrastructural, molecular, and real-time physiological assays using the xCelligence® RTCA CardioECR system, the inventors show that ARVC hiPSC-derived cardiac cell phenotypes can basally capture varying (electrical versus structural) cardiac disease phenotypes observed in heart tissue of donor ARVC patients. Through candidate gene approaches exploiting the xCelligence® RTCA CardioECR system in the inventors' ARVC hiPSC lines the inventors have also uncovered new therapeutics that can commonly reverse cardiac physiological defects underlying both electrical and structural forms of ARVC.

The present invention is based on the seminal discovery that restoring connexin 43 alone (to levels closer to healthy controls) in the face of a structurally compromised heart (via a one shot cardiac-targeted gene therapy) is sufficient for a positive therapeutic outcome. The studies described herein suggest that connexin 43 is a primary driver of structural based cardiac disease progression where cardiac muscle cell structural integrity is compromised. Given that connexin 43 is found between cardiac muscle cells and cardiac fibroblasts as well as cardiac muscle cells and cardiac macrophages, structural connections to these other associated cell types may also be compromised in a structurally diseased heart, and thus, connexin 43 restoration may also restore structural integrity of these cell-cell interactions. This is an unexpected finding as connexin 43 has never been considered as a therapeutic in the context of a structurally compromised heart.

In specific examples, the therapeutic methods described herein are targeted primarily towards the rare arrhythmogenic cardiac disease, arrhythmogenic right ventricular cardiomyopathy, which is a cardiac disease where mechanical cell-cell junctions of the desmosome are falling apart/lost and connexin 43 is an early hallmark of the disease. It is believed that connexin 43 restoration may only alleviate the early electrical defects in ARVC hiPSC derived cardiomyocytes that harbored electrical defects. Results shown herein were surprising in late stage structural models of ARVC shown herein. Using ARVC hiPSC derived cardiomyocytes with structural hallmarks of disease (human in vitro model) as well as a genetic mouse model mimicking a severe structural form of ARVC (DSP cKO mouse in vivo model), the data revealed that even though a major mechanical (desmosomal) cell-cell junction gene is ablated/mutated and other associated desmosomal cell-cell junction proteins are falling apart/lost, that connexin 43 gene therapy was effective in improving survival, heart rhythm and function in (late) structural stages of ARVC disease. Further, it is believed that the invention methods can now be extended to other forms of structurally compromised forms of heart diseases, such as hypertrophic cardiomyopathy and congestive heart failure as there is evidence in the literature that connexin 43 is also lost at late stages in these diseases, and it is at these late stages when lethal arrhythmias and structural integrity of cardiac muscle (and its associated cell interactions) is most compromised.

ARVC is a predominantly genetic-based heart disease characterized by right, but also recently left, ventricular dysfunction, and fibro-fatty replacement of the myocardium resulting in fatal/severe ventricular arrhythmias leading to sudden cardiac death in young people and athletes. ARVC is responsible for 10% of sudden cardiac deaths in people 65 years of age and 24% in people 30 years of age. ARVC is thought to be a rare disease as it occurs in 1 in 1000-5000 people, although the prevalence may be higher as some patients are undiagnosed or misdiagnosed due to poor diagnostic markers. Growing evidence also reveals earlier onset since pediatric populations ranging from infants to children in their teens are also particularly vulnerable to ARVC, highlighting the critical need to identify and treat patients at an earlier stage of the disease.

At present there are no effective treatments for ARVC and there has been no randomized trial of treatment modalities, screening regimens, or medications specific for ARVC. As a result, treatment strategies for ARVC patients are directed at symptomatic relief of electrophysiological defects, based on clinical expertise, results of retrospective registry-based studies, and the results of studies on model systems. As a result, existing therapies for ARVC patients rely upon the use of anti-arrhythmic drugs (sotalol, amiodarone, and beta-blockers) that transition into more invasive actions, which include implantable cardioverter defibrillators and cardiac catheter ablation, if the patient becomes unresponsive or intolerant to anti-arrhythmic therapies. However, current therapeutic modalities have limited effectiveness in managing the disease as 40% of ARVC patients die within 10-11 years after initial diagnosis, highlighting the need for the development of more effective therapies for patients with ARVC.

Disclosed herein is a gene therapy strategy to rescue/treat cardiac electrical and physiological dysfunction in the arrhythmogenic disorder, ARVC, via targeted overexpression of connexin 43 polypeptide in cardiac muscle cells using vector delivery strategies. In an illustrative example described herein, a one-time viral-mediated delivery of connexin 43 polynucleotide encoding connexin 43 polypeptide to heart muscle cells of two ARVC hiPSC patient lines in vitro and a novel mouse model of ARVC in vivo was sufficient to substantially reverse the cardiac electrical and physiological dysfunction associated with ARVC. An in vivo study using the DSP-cKO mouse model of ARVC further suggests that the connexin 43 gene therapy treatment strategy can be exploited during late-stage disease states to prolong life by circumventing the sudden death associated with ARVC. This strategy can also have treatment applications to other genetic disorders that give rise to arrhythmic sudden death (e.g., hypertrophic cardiomyopathy) as well as late stages of heart failure, where there is increased risk of arrhythmias and death as well as where loss of connexin 43 polypeptide has been reported. The studies further suggest that connexin 43 polypeptides may have a role beyond electrical function and also act as a scaffold to bridge structural connections between cells (independent of classic structural proteins, such as desmosomal proteins) as cardiac function could also be improved in the inventors' models with severe structural disease (e.g., structural ARVC hiPSC line ($PKP2_{mut}$) and the mouse model of ARVC), which is distinct from previous thoughts of the role of this protein in the field as classically associated with electrical function only.

As used herein "overexpression" refers to an increased level of expression as compared to the disease state, and in particular embodiments in comparison with the absent or minimal level of connexin 43 polypeptide expression found in a disease state, and not as compared to a normal, healthy or wild-type state. Restoration of connexin 43 polypeptide expression levels to at least about 5% of normal are beneficial, if not necessarily fully restorative of cardiac function. Restoration of connexin 43 expression levels to 5%, 10%, 15%, 20%, 25% or as much as 50% of normal levels are effective for restoring normal cardiac function.

As used herein, the term "vector" has its ordinary meaning in the field and includes the understanding that it is capable of transferring nucleic acid sequences to target cells. For example, a vector may comprise a coding sequence capable of being expressed in a target cell. For the purposes of the present disclosure, "vector construct," "expression vector," and "gene transfer vector," generally refer to any nucleic acid construct capable of directing the expression of a gene of interest and which is useful in transferring the gene of interest into target cells. Thus, the term includes cloning and expression vectors, as well as integrating vectors.

As used herein, the term "adeno-associated virus" (AAV) has its ordinary meaning in the field and includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV2i8, (Asokan et al., *Nat Biotechnol.* (1):79-82, 2010, which is incorporated herein by reference in its entirety) avian AAV, bovine AAV, canine AAV, equine AAV, and ovine AAV and any other AAV now known or later discovered. A number of additional AAV serotypes and clades have been identified, which are also encompassed by the term "AAV."

The genomic sequences of various AAV and autonomous parvoviruses, as well as the sequences of the inverted terminal repeats (ITRs), Rep proteins, and capsid subunits are known in the art. Such sequences may be found in the literature or in public databases such as the GenBank® database.

As used herein, the terms "cardiomyocyte" or "cardiac myocyte" have their ordinary meaning in the field and include a specialized muscle cell that primarily forms the myocardium of the heart. Cardiomyocytes can have five major components: (1) cell membrane (sarcolemma) and T-tubules, for impulse conduction, (2) sarcoplasmic reticulum, a calcium reservoir needed for contraction, (3) contractile elements, (4) mitochondria, and (5) a nucleus. Cardiomyocytes can be subdivided into subtypes including, but not limited to, atrial cardiomyocyte, ventricular cardiomyocyte, sinoatrial (SA) nodal cardiomyocyte, peripheral SA nodal cardiomyocyte, or central SA nodal cardiomyocyte. Stem cells can be propagated to mimic the physiological functions of cardiomyocytes or alternatively, differentiate into cardiomyocytes. This differentiation can be detected by the use of markers selected from, but not limited to, myosin heavy chain, myosin light chain, actinin, troponin, tropomyosin, GATA4, myocyte enhancer factor (Mef)2c, and Nkx-2.5.

As used herein, the term "control" has its ordinary meaning in the field and includes an alternative subject or sample used in an experiment for comparison purpose. A control can be "positive" or "negative." For example, where the purpose of the experiment is to determine a correlation of an altered expression level of a gene with a particular phenotype, it is generally preferable to use a positive control (a sample from a subject, carrying such alteration and exhibiting the desired phenotype), and a negative control (a subject or a sample from a subject lacking the altered expression or phenotype).

As used herein, the term "stem cell" has its ordinary meaning in the field and includes a cell that is in an undifferentiated or partially differentiated state and has the capacity for self-renewal and/or to generate differentiated progeny. Self-renewal is defined as the capability of a stem cell to proliferate and give rise to more such stem cells, while maintaining its developmental potential (i.e., totipotent, pluripotent, multipotent, etc.). As used herein, the term "somatic stem cell" has its ordinary meaning in the field and includes any stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally-occurring somatic stem cells include, but are not limited to, mesenchymal stem cells (MSCs) and neural stem cells (NSCs). In some embodiments, the stem or progenitor cells can be embryonic stem cells. As used herein, the term "embryonic stem cells" has its ordinary meaning in the field and includes stem cells derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Most frequently, embryonic stem cells are pluripotent cells derived from the early embryo or blastocyst. Embryonic stem cells can be obtained directly from suitable tissue, including, but not limited to human tissue, or from established embryonic cell lines. As used herein, the term "embryonic-like stem cells" has its ordinary meaning in the field and includes cells that share one or more, but not all characteristics, of an embryonic stem cell.

As used herein, the term "pluripotent cell" has its ordinary meaning in the field and includes a less differentiated cell that can give rise to at least two distinct (genotypically and/or phenotypically) further differentiated progeny cells. In some embodiments, a "pluripotent cell" includes an Induced Pluripotent Stem Cell (iPSC) which is an artificially derived stem cell from a non-pluripotent cell, typically an adult somatic cell, that have been produced by inducing expression of one or more stem cell-specific genes. Such stem cell specific genes include, but are not limited to, the family of octamer transcription factors, i.e. Octomer-binding transcription factor binding (Oct)-3/4; the family of SRY Box (Sox) genes, i.e., Sox1, Sox2, Sox3, Sox 15, and Sox 18; the family of Kruppel-like factor (Klf) genes, i.e. Klf1, Klf2, Klf4, and Klf5; the family of Myc genes, i.e. c-myc and L-myc; the family of Nanog genes, i.e., OCT4, NANOG, and REX1; or LIN28.

As used herein, the term "induced pluripotent cell" has its ordinary meaning in the field and includes embryonic-like cells reprogrammed to the immature phenotype from adult cells. Human iPSCs also express stem cell markers and are capable of generating cells characteristic of all three germ layers.

As used herein, the term "effective amount" has its ordinary meaning in the field and includes a concentration or amount of a reagent or composition, such as a composition as described herein, a viral or other vector, that is effective for producing an intended result, including cell growth and/or differentiation in vitro or in vivo, or for the treatment of a condition as described herein. It will be appreciated that the amount of viral or other vector to be administered will vary depending on the specifics of the disorder to be treated, including but not limited to size or total volume/surface area to be treated, as well as proximity of the site of administration to the location of the region to be treated, among other factors familiar to the medicinal biologist.

As used herein, the term "arrhythmogenic right ventricular cardiomyopathy" (ARVC) has its ordinary meaning in the field and includes an inherited progressive disorder that usually affects the right side of the heart but it can affect both sides. The walls of the ventricle become thin and stretched. ARVC can also cause abnormal heart rhythms.

As used herein, the term "hypertrophic cardiomyopathy" has its ordinary meaning in the field and includes a situation where the heart muscle cells enlarge and cause the ventricles to thicken.

As used herein, the term "connexin 43" has its ordinary meaning in the field and includes a gap junction protein. Gap junctions can be essential for many physiological processes, such as the coordinated depolarization of cardiac cells, proper embryonic development, and the conducted response in microvasculature. For this reason, mutations in connexin-encoding genes can lead to functional and developmental abnormalities. The amino acid sequence of the human protein is found under Genbank Accession number AAA52131. The amino acid sequence of the murine protein is found under Accession number AAA37444. The amino acid sequence of the canine protein is found under Accession number AAR25626. The amino acid sequence of the equine protein is found under Accession number NP_001296155.

The presently disclosed methods comprise a viable treatment strategy that has implications in prolonging life by rescuing the cardiac electrical and physiological dysfunction associated with arrhythmogenic disorders, such as ARVC. To date, there are no existing treatments that exploit connexin 43-based treatments or gene therapy treatments for ARVC patients. Currently disclosed connexin 43-based strategies are focused on using peptide mimetics and small molecule drugs, which primarily act to re-localize the existing connexin 43 from the cell to the "correct location;" these strategies rely on having existing connexin 43 protein in the heart. However, ARVC patients and end-stage heart failure patients have extremely little or no connexin 43 protein in heart muscle cells, thus these approaches do not work in these settings.

Gene therapy has been shown to be safe and effective approach to circumvent cardiac disease, and the experiments presented herein provide evidence that this method can restore connexin 43 expression in the heart as well as circumvent the electrical and structural defects associated with ARVC that drive sudden death. Since ARVC is a rare and fatal disease with no treatment, this approach will provide the first opportunity to test treatment approaches in this very vulnerable population, and this strategy may also have applications to other cardiac diseases that have underlying structural and arrhythmogenic defects associated with the loss of connexin 43 polypeptide.

Thus, in some embodiments, connexin 43 polypeptide is targeted for clinical therapies for ARVC patients by generating a cardiac troponin T promoter-driven adeno-associated viral vector (serotype 9) containing the human connexin 43 cDNA and amplifying and delivering clinical grade virus to ARVC patients as a means to restore connexin 43 protein levels as well as rescue electrical and contractile dysfunction. However, in some embodiments other vectors are used. In some embodiments the vector uses a different promoter. While the promoter must be active in cardiac tissue, the promoter can be, but is not necessarily, only or primarily active in cardiac tissue. In some embodiments the vector is an adeno-associated viral vector. In some embodiments the vector is based on a different virus. In some embodiments the vector is non-viral.

In some cases, the vector is a viral vector. In some cases, the viral vector is based on, or derived from, a replication-deficient virus. Non-limiting examples of viral vectors suitable for delivering a nucleic acid molecule of the disclosure to a subject include those derived from adenovirus, retrovirus (e.g., lentivirus), adeno-associated virus (AAV), and herpes simplex-1 (HSV-1). In a particular case, the viral vector is derived from AAV.

In some embodiments the vector has a tropism for cardiac tissue, such as adeno-associated virus serotype 9 (AAV9), but in other embodiments the vector is not specific for cardiac tissue. In some embodiments connexin 43 expression is restricted to cardiac tissue as a result of a tissue-specific promoter, or a cardiotropic vector, or both. In some embodiments the vector confers long-lasting expression of connexin 43 polypeptide. In some embodiments the vector is non-integrative.

In some embodiments effective treatment is accomplished with a single administration of a gene therapy vector. In such embodiments, weak or non-immunogenicity is of reduced importance as compared to vectors that might be, or are expected to be, administered more than once. In some embodiments the vector is one to which the recipient does not have a pre-existing immune response, for example, an anti-vector antibody response.

This strategy can also have treatment applications to other genetic disorders that give rise to arrhythmic sudden death (e.g., hypertrophic cardiomyopathy) as well as late-stage heart failure, where there is increased risk of arrhythmias and death as well as where loss of connexin 43 has been reported.

Provided herein are methods for treating a disease or disorder in a subject in need thereof, wherein the subject is suffering from one or more of: arrhythmogenic right ventricular cardiomyopathy; right and/or left ventricular dysfunction; fibro-fatty replacement of the myocardium; hypertrophic cardiomyopathy; cardiac electrical and physiological dysfunction in arrhythmogenic disease. The method comprises, or alternatively consists essentially of, or yet further consists of, administering to the subject a vector encoding a connexin 43 polypeptide sequence, wherein as a result of the administration of an effective amount of the vector, connexin 43 levels in at least a portion of the heart of the subject are increased. Increased connexin 43 polypeptide is typically inferred by improvements in symptomology. In some embodiments improvements in symptomology can be seen within days of expression of connexin 43 being increased or within days of a connexin 43 gene therapy vector being administered, for example, within 1, 2, 3, or 4 days.

In some embodiments, the connexin 43 polypeptide comprises at least a 382 amino acid sequence of P17302 (CXA_1HUMAN; UniProtKB) (SEQ ID NO. 1), or a biological equivalent thereof. There are at least four smaller truncated isoforms of connexin 43 in human heart, which include the 32 kDa (100-382AA; SEQ ID NO: 3), 29 kDa (125-382AA; SEQ ID NO: 4), 26 kDa (147-382AA; SEQ ID NO: 5) and 20 kDa (213-382AA; SEQ ID NO: 6), that may act as functional fragments thereof (Autoregulation of connexin43 gap junction formation by internally translated isoforms, Smith & Shaw, Cell Rep. 5(3):611-8, 2013, which is incorporated by reference herein in its entirety). In some embodiments there fragments are encoded by SEQ ID NOS: 9 to 12, respectively.

The polypeptide can be delivered in a gene delivery vehicle or construct, comprising the polynucleotide encoding connexin 43 operatively linked to sequences for expression of the polynucleotide in vivo. Non-limiting examples of such include, for example a cardiac troponin T promoter, cardiac myosin light chain promoter, cardiac myosin heavy chain promoter, and an α-cardiac actin enhancer attached to an elongation factor 1 α promoter. Cardiomyocyte-specific spatially restricted promoters include, but are not limited to control sequences derived from the following genes: myosin light chain-2, alpha-myosin heavy chain, AE3, cardiac troponin C, cardiac actin, and the like.

The constructs can be further contained within a viral vector; non-limiting examples of such include an adenoviral vector, an adeno-associated vector (AAV), or a lentiviral vector. The viral vector can be selected for tissue tropism to the heart, e.g., an AAV vector from the group of an AAV1, AAV2, AAV2i8, or an AAV9 serotype, (see An Emerging Adeno-Associated Viral Vector Pipeline for Cardiac Gene Therapy, Asokan and Samulski, Hum Gene Ther. 24(11): 906-913, 2013, and *Systemic Gene Transfer to Skeletal Muscle Using Reengineered AAV Vectors*, Phillips et al., Methods Mol Biol. 709:141-51, 2011, each of which is incorporated herein by reference in its entirety for all that is teaches about in vivo cardiac gene transfer). In addition, the AAV vector can be chimeric, further adding to the tissue tropism of the vector. Non-limiting examples of such include, for example, AAV1/2 vectors described in *AAV Vectors for Cardiac Gene Transfer: Experimental Tools and Clinical Opportunities* (Mol. Ther. 19(9):1582-1590, 2011), which is incorporated herein by reference in its entirety for all that is teaches about in vivo cardiac gene transfer.

The vectors containing the connexin 43 polynucleotide are administered locally or systemically.

The methods are useful for the treatment of mammals, such as a human patient. As is understood by one of skill in the art, the protein and/or polynucleotide will be from the same species of the subject being treated.

An effective amount of the polynucleotide and/or vector should be delivered, e.g., from about $2 \times 10^{11}$ to about $2 \times 10^{14}$ viral genomes per kg of body weight of the subject. The vectors can be delivered in pharmaceutically acceptable carriers.

Also provided are methods for treating a subject in need thereof, wherein the subject is suffering from one or more of: arrhythmogenic right ventricular cardiomyopathy; right and/or left ventricular dysfunction; fibro-fatty replacement of the myocardium; hypertrophic cardiomyopathy; or cardiac electrical and physiological dysfunction in arrhythmogenic disease. The methods comprise, or alternatively consist essentially of, or yet further consist of, administering to the subject an effective amount of a vector conferring expression of connexin 43 polypeptide as herein disclosed. One of skill in the art can determine if connexin 43 levels are increased in model systems by immunohistochemistry, western blot, affinity chromatography, or indirectly based on detection of mRNA through northern blot, reverse transcriptase polymerase chain reaction (RT-PCR), and the like. In actual patients, detection of increased connexin 43 polypeptide is typically inferred by improvements in symptomology.

In some embodiments, the connexin 43 polypeptide comprises at least a 382 amino acid sequence of P17302 (CXA_1HUMAN; UniProtKB) (SEQ ID NO. 1), or a biological equivalent thereof.

Some embodiments are pharmaceutical compositions comprising a vector capable of conferring connexin 43 polypeptide expression and a pharmaceutically acceptable carrier. Pharmaceutically acceptable carriers for such product are typically sterile aqueous solutions. In various aspects of these embodiments the pharmaceutically acceptable carrier can comprise culture media, phosphate-buffered saline, or HEPES-buffered saline. In some embodiments the vector is supplied in a liquid formulation, which may be stored frozen, for direct use. In other embodiments the vector is supplied in freeze-dried form and reconstituted shortly prior to administration with water-for-injection or a sterile aqueous solution.

Several of the disclosed embodiments comprise administration to a mammal, for example a human, and constitute method of treatment. As used herein the term "treating" or "treatment" broadly includes, both collectively and as individual embodiments, any kind of treatment activity, including the diagnosis, mitigation, or prevention of disease in man or other animals, or any activity that otherwise affects the structure or any function of the body of man or other animals. Treating can include obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder, e.g., cardiac arrhythmia. As is understood by those skilled in the art, "treatment" can include systemic amelioration of the symptoms associated with the pathology and/or a delay in onset of symptoms such as chest pain. Clinical and subclinical evidence of "treatment" will vary with the pathology, the individual and the treatment. Treatment activity includes the administration of the medicaments, dosage forms, and pharmaceutical compositions described herein to a patient, especially according to the various methods of treatment disclosed herein, whether by a healthcare professional, the patient his/herself, or any other person. Treatment activities include the orders, instructions, and advice of healthcare professionals such as physicians, physician's assistants, nurse practitioners, and the like that are then acted upon by any other person including other healthcare professionals or the patient his/herself. In some embodiments, treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like.

In several of the herein disclosed embodiments, connexin 43 polypeptide expressing vectors are prepared for administration to a mammal or administered to a mammal. In some embodiments the mammal is a human. In other embodiments the mammal is a domestic pet, for example a cat or a dog. In some embodiments the mammal is an agricultural animal, for example, a horse, a cow, a sheep, or a hog. In other embodiments, the mammal is a laboratory animal, for example a mouse, a rat, a hamster, or a rabbit.

In a related aspect, the therapeutic compositions of the present invention are administered to a subject as a prophylactic or ameliorative modality. As used herein, "ameliorative," means to improve or relieve a subject of symptoms associated with a disorder, and includes curing such a disorder.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein.

Administration of gene therapy vectors is typically by injection or infusion. In some embodiments intravenous administration is used. In other embodiments the vectors are administered into a tissue, organ, or body cavity that is, or is in communication with, the site where treatment is to take effect; such as the heart itself, or the pericardial space.

Suitable doses of the vector can be administered to a subject in need thereof. Non-limiting examples of methods of administration include subcutaneous administration, intravenous administration, intramuscular administration, intradermal administration, intraperitoneal administration, oral administration, infusion, intracranial administration, intrathecal administration, intranasal administration and intra-arterial. In some cases, administration can involve injection of a formulation of the vector composition.

Continuous and discontinuous administration schedules by any method also include dosing schedules in which the dose of vector is modulated throughout the effective period, such that, for example, at the beginning of the connexin 43 administration period; the dose is low and increased until the end of the connexin administration period; the dose is initially high and decreased during the administration period; the dose is initially low, increased to a peak level, then reduced towards the end of the administration period; and any combination thereof. Also, the dosing schedules may be performed using any method of standard in the art, such as a catheter system.

Recombinant AAV (rAAV) virions or cells transduced in vitro may be delivered directly to muscle by injection with a needle, catheter or related device, using techniques known in the art. For in vivo delivery, the rAAV virions will be formulated into pharmaceutical compositions and one or more dosages may be administered directly in the indicated manner. A therapeutically effective dose will include on the order of from about $10^8$/kg to $10^{16}$/kg of the rAAV virions, more preferably $10^{16}$/kg to $10^{14}$/kg, and even more preferably about $10^{11}$/kg to $10^{13}$/kg of the rAAV virions (or viral genomes, also termed "vg" or "v.g."), or any value within these ranges.

One mode of administration of recombinant AAV virions uses a convection-enhanced delivery (CED) system. In this way, recombinant virions can be delivered to many cells over large areas of muscle. Moreover, the delivered vectors efficiently express transgenes in muscle cells. Any convection-enhanced delivery device may be appropriate for delivery of viral vectors. In a preferred embodiment, the device is an osmotic pump or an infusion pump. Both osmotic and infusion pumps are commercially available from a variety of suppliers, for example Alzet Corporation, Hamilton Corporation, Alza, Inc. (Palo Alto, CA). Typically, a viral vector is delivered via CED devices as follows. A catheter, cannula or other injection device is inserted into appropriate muscle tissue in the chosen subject, such as skeletal muscle. For a detailed description regarding CED delivery, see U.S. Pat. No. 6,309,634, incorporated herein by reference in its entirety.

Various perfusion methods are available and standard in the art, and without being held to any one method, any perfusion method which gives the desired result is contemplated, such as methods utilizing a catheter. The objective of the perfusion methods is to increase the time of contact between the vector (e.g., adenovirus, AAV, lentivirus vectors) and the target cells (e.g., smooth muscle cells). Hence, the method encompasses perfusion methods such as closed-circuit perfusion methods carried out at body temperature, and under defined conditions at, for example, 37 degrees C., for about 2, 5, 10, 12, 15, 30, 60 or more minutes, or in larger animals or humans for about 2, 4, 6, 8, 10, 12 or more hours, allowing viral entry into the target cells and to create optimal conditions for gene expression and protein synthesis. For this reason, various excipients, e.g., natural and un-natural amino acids, growth factors and the like may be added to provide enough material for protein synthesis.

Each method of treatment may be expressed as a composition(s) for use in such a medical method. For example, embodiments comprising a connexin 43 polypeptide expressing vector for use in treating an arrhythmogenic disease. Similarly, each method of treatment may be expressed as a composition(s) for use in the manufacture of a medicament. For example, a connexin 43 polypeptide expressing vector for use in the manufacture of a medicament for treating an arrhythmogenic disease.

The present invention is more particularly described in the following examples which are intended as illustrative only since numerous modifications and variations therein will be apparent to those skilled in the art. The following examples are intended to illustrate but not limit the invention.

EXAMPLES

Example 1

Increased Connexin 43 Expression Promoted Prolonged Life and Restoration of Cardiac Rhythm and Function in a Genetic Model of Cardiomyopathy Connexin 43 was lost in arrhythmogenic right ventricular cardiomyopathy hiPSC-derived cardiomyocytes that displayed abnormal electrical, structural, and contractile activity as well as cardiac connexin 43 was lost early on in a mouse model of ARVC that exhibits cardiac dysfunction and sudden death. Attempts at re-localizing the existing connexin 43 that was left in the cell using a connexin 43 carboxy terminus mimetic alpha-carboxy terminus 1 (CT1) peptide and rotigaptide failed, which suggested that there is not enough connexin 43 and thus genetic restoration of connexin 43 would be required to restore its levels and function.

Figure 1G:
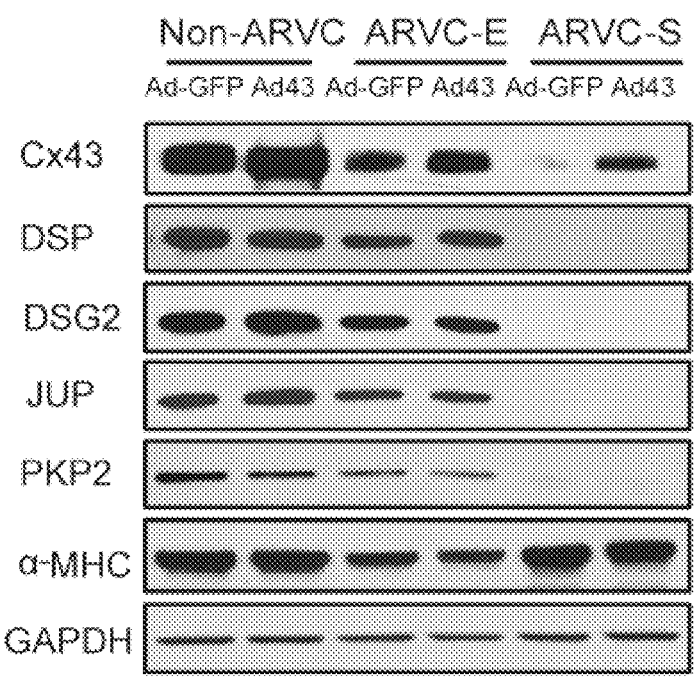
Figure 3E:
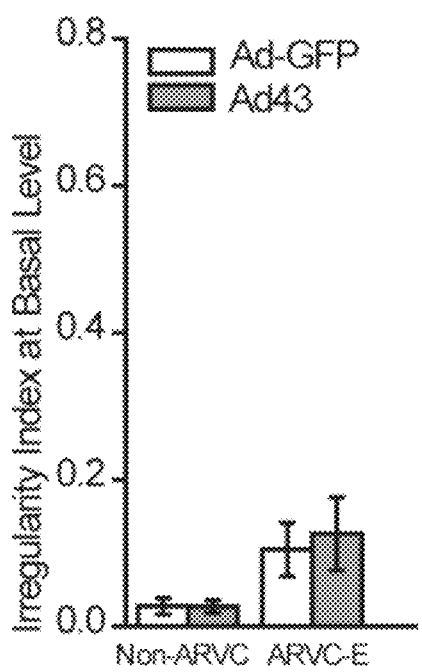
Figure 3F:
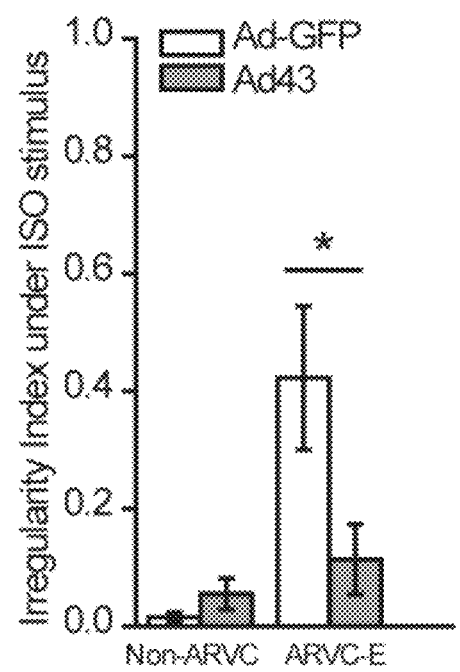

Using the Cx43 YFP adenovirus, the present inventors showed that connexin 43 overexpression is sufficient to restore normal cardiomyocyte rhythm (as measured via field potential) and contractile function (as measured via impedance) in a severely structurally abnormal human ARVC patient iPSC cell line carrying the PKP2 c.1171-2A>G ($PKP2_{mut}$) (FIG. 1A-F). Western blot analysis revealed that connexin43 overexpression was sufficient on its own to rescue functional alterations in the ARVC ($PKP2_{mut}$) without impacting desmosomal (mechanical cell-cell junction) proteins that were shown to be lost in this ARVC hiPSC line (FIG. 1G). Nonetheless, in some embodiments connexin 43 gene therapy can be used in conjunction with adjunctive therapies directed at desmosomal protein restoration to further reinforce the cell-cell junction in ARVC.

Using the Cx43 YFP adenovirus, the present inventors also showed that the rescued effects of connexin43 overexpression in the structural ARVC ($PKP2_{mut}$) hiPSC line were dose-dependent (FIG. 2).

Using the Cx43 YFP adenovirus, the present inventors showed that connexin 43 overexpression could also rescue the catecholamine induced arrhythmias and dysfunction in an electrical ARVC hiPSC line carrying the DSG2 c.1498 C>A ($DSG_{mut}$) following isoproterenol stimulation (FIG. 3A-F).

Figure 4A:
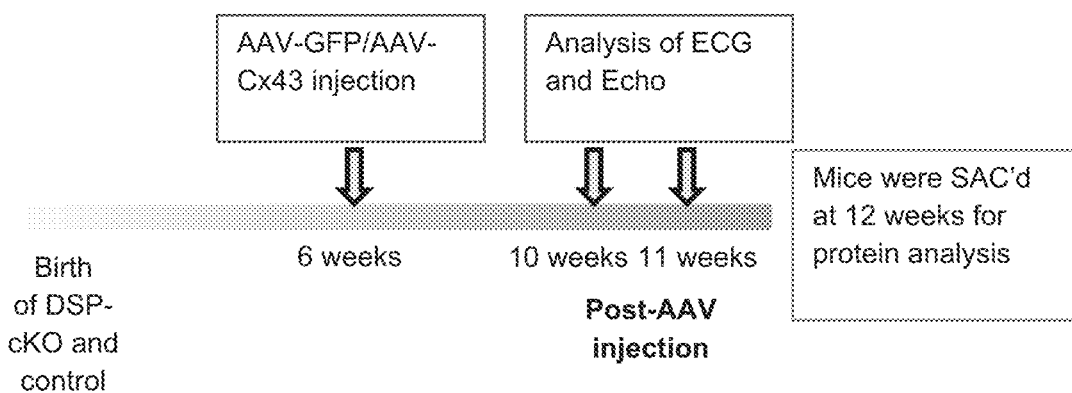
FIGS. 4A-4G depict that restoration of connexin 43 protein levels can improve heart rhythm and function in an ARVC mouse model (cardiac-specific desmoplakin knockout model ((DSP-cKO).
Figure 4B:
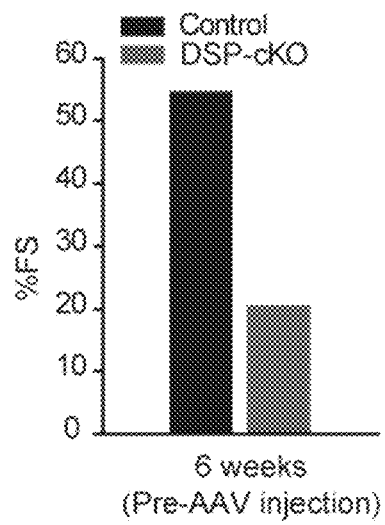
Figure 4C:
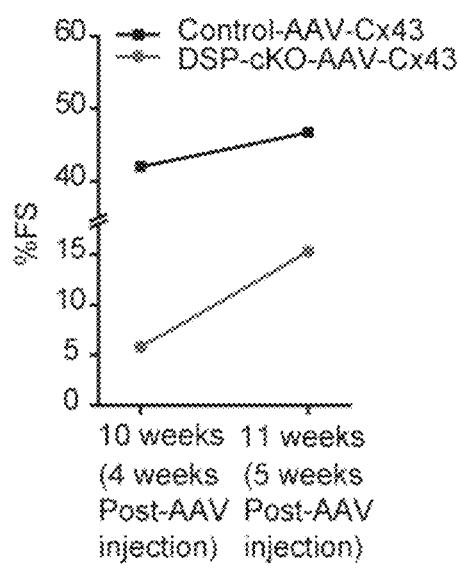
Figure 4D:
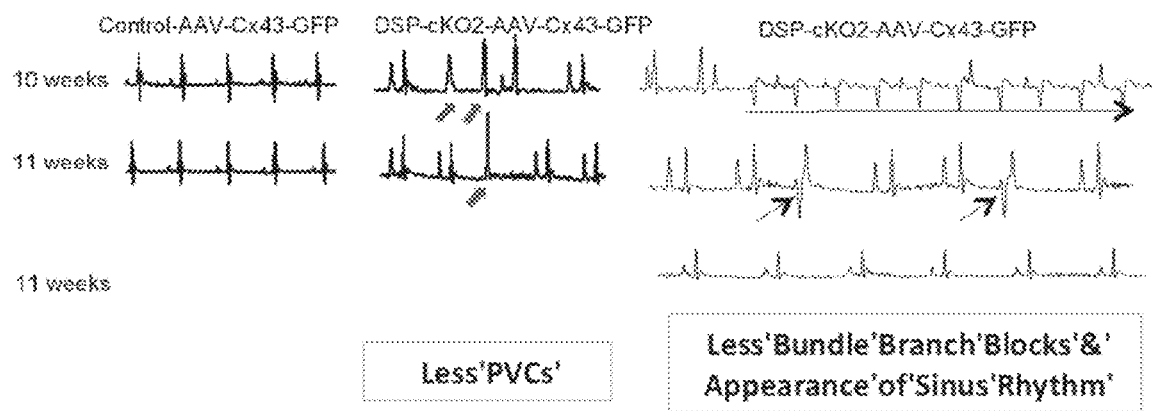
Figures 4E, 4F:
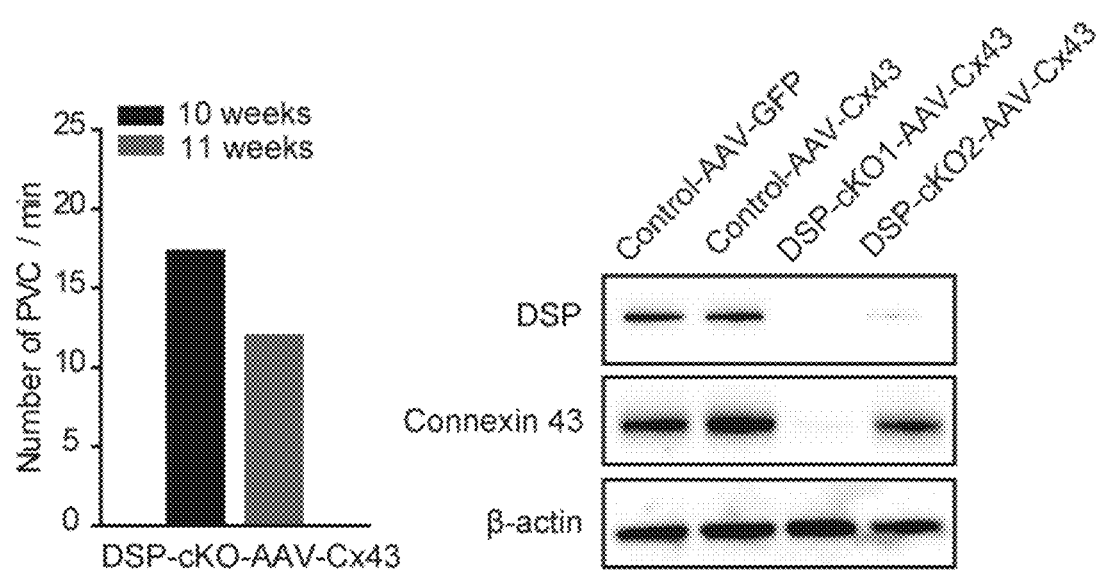
Figure 4H:
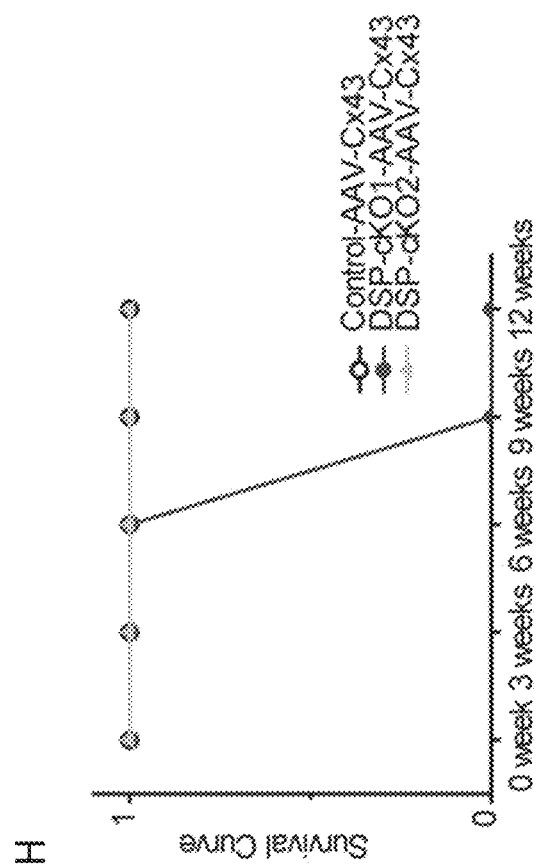
Figure 4G:
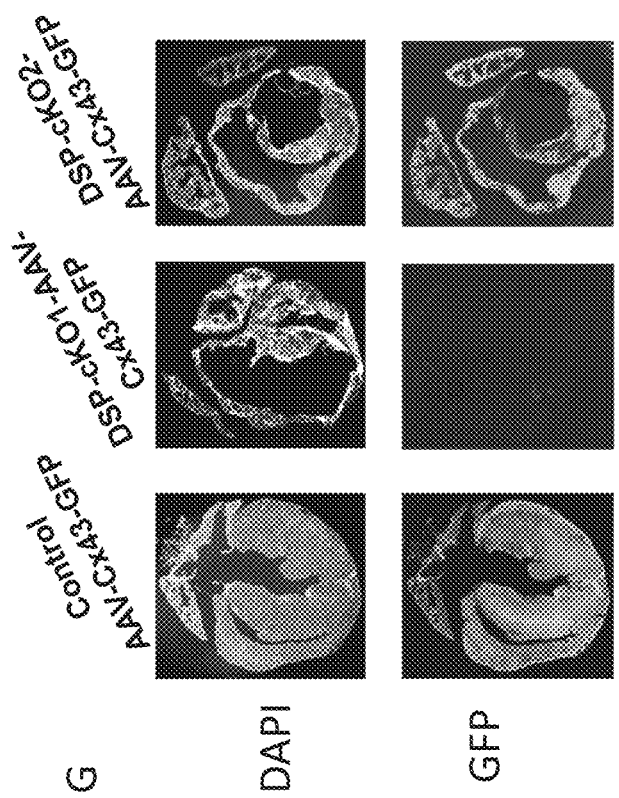
Figure 5:
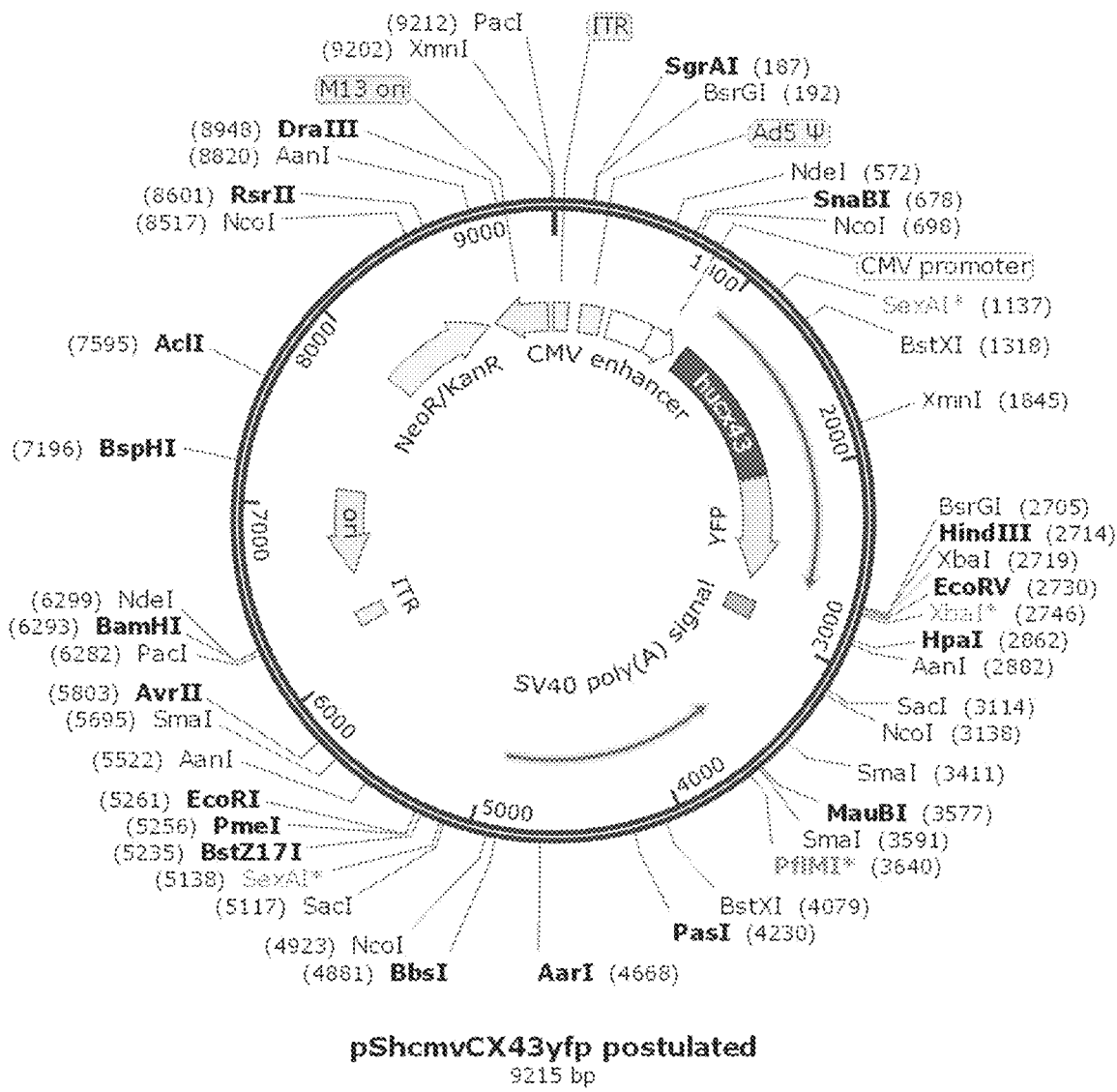
FIG. 5 depicts a vector map of Ad43 (SEQ ID NO: 7).
Figure 6:
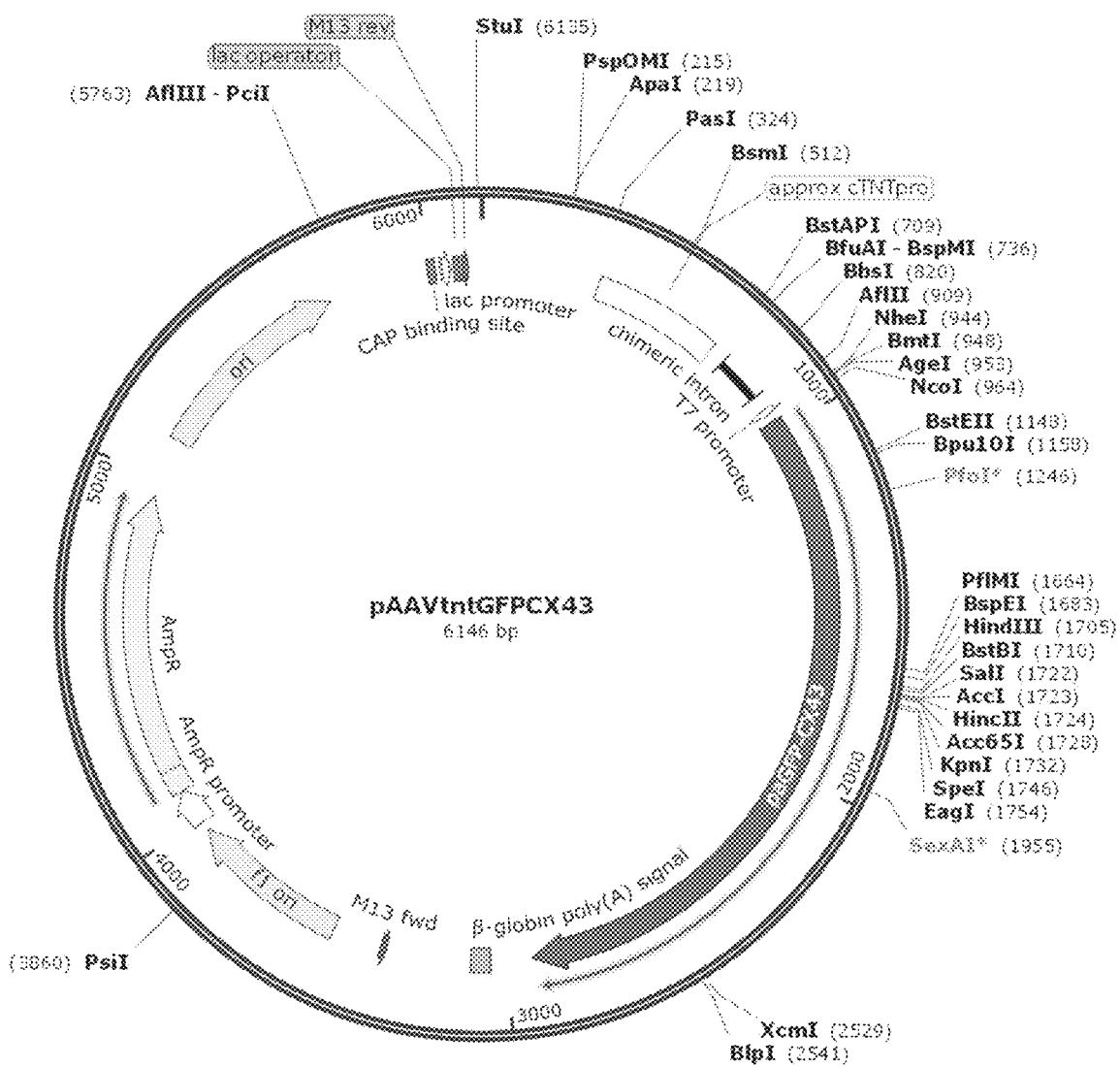
FIG. 6 depicts a vector map of AAV-Cx43 (SEQ ID NO: 8).

Using the Cx43 GFP adeno-associated virus (AAV) construct, one time gene delivery of Cx43 GFP AAV can prolong life (by 2-fold) and improve cardiac function (by 2.5-fold) and rhythm (by 1.5-fold) in an adult mouse model of ARVC (DSP-cKO), that undergoes premature sudden death (FIG. 4A-H). The DSP-cKO mouse model has been described previously. An adult DSP-cKO mouse injected with the Cx43 GFP AAV was found dead at 3 weeks post-AAV injection; however, western blot analyses revealed that this mouse did not successfully express Cx43 in the heart (likely did not have enough time to express), further reinforcing that it was Cx43 overexpression that was key to the prolonged life and restoration of cardiac rhythm and function in surviving DSP-cKO mice (FIG. 4H).

The present inventors have tested the proof of concept prototype in vitro using a human connexin 43-yellow fluorescent protein tagged adenovirus driven by the human cytomegalovirus (CMV) immediate early enhancer/promoter in human iPSC-derived cardiomyocytes from two ARVC patient lines that exhibit primarily electrical (catecholamine-induced defects) as well as combined structural/electrical characteristics. Restoration of connexin 43 to control levels was sufficient to rescue both catecholamine-induced electrical and contractile deficits in the inventors' electrical ARVC hiPSC line as well as basal and catecholamine-induced electrical and contractile deficits in the inventors' combined structural and electrical ARVC hiPSC line (FIGS. 1-3). The present inventors have also generated a cardiac troponin T-driven adeno-associated virus (cardiotropic serotype 9) harboring human connexin 43 and tagged with green fluorescent protein to show that the virus can be successfully delivered and express in a late-stage diseased mouse heart harboring ARVC (DSP-cKO mice) using a one time delivery method (retro-orbital delivery). The present inventors also showed that the Cx43 AAV likely takes between 3-6 weeks at a dose of $2.4 \times 10^{11}$ viral genomes/mouse for it to be optimally expressed based on the DSP cKO mouse that received the virus and died (3 weeks post AAV injection, showing no connexin 43 protein expression) versus the DSP cKO mouse that received the virus and survived (6 weeks post AAV injection, showing robust connexin 43 protein expression) (FIG. 4). The present inventors further show that DSP cKO mouse that received the virus and showed robust connexin 43 protein expression lived longer (by 2 fold) and demonstrated improved cardiac function (by 2.5 fold) and rhythm (by 1.5 fold) (FIG. 4). The present inventors also show that this AAV virus does not impact cardiac electrical and contractile function in control mice, throughout the duration of the study (sacrifice occurred at 5 weeks post-AAV injection) (FIG. 4).

Example 2

Increased Cx43 Expression Promotes Prolonged Life and Restoration of Cardiac Rhythm and Function in an Injury Model of Cardiac Hypertrophy Six to eight week old mice undergo transverse aortic constriction for 4 weeks to induce pressure overload induced cardiac hypertrophy and heart failure. The mice are administered Cx43 gene therapy after this 4 week period via a one-time retro-orbital vein injection at similar doses to the ARVC model used in Example 1 (above). Mice are monitored continuously for 1, 2 and 4 weeks via echocardiography and telemetry to monitor left ventricular function and heart rhythm, respectively. As compared to controls AAV Cx43 treated mice have improved cardiac function, such as fractional shortening, reduction in rhythm abnormalities, such as less PVCs, as well as improved survival. Histological analysis is performed to assess heart size and fibrotic infiltration into the heart muscle post infection. The AAV Cx43 treated mice display reduced heart size (as well as cardiac dimensions) and less fibrosis following pressure overload when compared to controls.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the embodiments of the present disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the subject matter herein (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate embodiments discussed herein and does not pose a limitation on the scope of the subject matter otherwise claimed. No language in the specification should be construed as indicating any non-claimed element essential to the practice of any of the embodiments discussed herein.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors of this disclosure for carrying out the inventive subject matter disclosed herein. Of course, variations on these described embodiments will become apparent to those of ordinary skill in the art upon reading the foregoing description. The inventors expect skilled artisans to employ such variations as appropriate, and the inventors intend for the present subject matter to be practiced otherwise than specifically described herein. Accordingly, this scope of the disclosed subject matter includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments discussed herein and so claimed are inherently or expressly described and enabled herein.

Furthermore, numerous references have been made to patents and printed publications throughout this specification. Each of the above-cited references and printed publications is individually incorporated herein by reference in their entirety.

In closing, it is to be understood that the embodiments disclosed herein are illustrative of the principles of the present subject matter. Other modifications that may be employed are within the scope of this disclosure. Thus, by way of example, but not of limitation, alternative configurations may be utilized in accordance with the teachings herein. Accordingly, the disclosed subject matter and the claimed inventions are not limited to that precisely as shown and described.

What is claimed is:

1. A method for treating arrhythmogenic right ventricular cardiomyopathy (ARVC) in a subject in need thereof, comprising systemically administering to the subject an adeno-associated virus (AAV) vector encoding a connexin 43 polypeptide sequence operably linked to a promoter that is active in cardiac muscle tissue such that connexin 43 polypeptide levels in at least a portion of the heart of the subject are increased.

2. The method according to claim 1, wherein the connexin 43 polypeptide sequence comprises a 382 amino acid sequence of SEQ ID NO: 1, or a functional fragment thereof.

3. The method of claim 2, wherein the sequence encoding the connexin 43 polypeptide is SEQ ID NO: 2.

4. The method of claim 1, wherein the AAV vector is from the group of an AAV1, AAV2 or an AAV9 serotype.

5. The method according to claim 1, wherein the promoter is a cardiac-specific promoter.

6. The method according to claim 5, wherein the promoter is a troponin-T promoter.

7. The method according to claim 1, wherein the subject is a mammal.

8. The method of claim 7, wherein the subject is a human.

9. The method according to claim 1, wherein the effective amount is from about $2 \times 10^{11}$ to about $2 \times 10^{14}$ viral genomes of the AAV vector per kg of body weight of the subject.

10. The method according claim 1, wherein as a result of the administration, cardiac electrical dysfunction is reduced.

11. The method according to claim 1, wherein as a result of the administration, cardiac physiologic dysfunction is reduced.

12. The method of according to claim 1, wherein as a result of the administration, cardiac structural integrity is improved.

* * * * *

SEQUENCE LISTING

```
<160> NUMBER OF SEQ ID NOS: 12

<210> SEQ ID NO 1
<211> LENGTH: 382
<212> TYPE: PRT
<213> ORGANISM: Homo sapiens

<400> SEQUENCE: 1

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
        195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240
```

```
Lys Gly Lys Ser Asp Pro Tyr His Ala Thr Ser Gly Ala Leu Ser Pro
            245                 250                 255

Ala Lys Asp Cys Gly Ser Gln Lys Tyr Ala Tyr Phe Asn Gly Cys Ser
        260                 265                 270

Ser Pro Thr Ala Pro Leu Ser Pro Met Ser Pro Pro Gly Tyr Lys Leu
    275                 280                 285

Val Thr Gly Asp Arg Asn Asn Ser Ser Cys Arg Asn Tyr Asn Lys Gln
290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
        355                 360                 365

Ser Arg Ala Ser Ser Arg Pro Arg Pro Asp Asp Leu Glu Ile
    370                 375                 380

<210> SEQ ID NO 2
<211> LENGTH: 1146
<212> TYPE: DNA
<213> ORGANISM: Homo sapiens

<400> SEQUENCE: 2
atgggtgact ggagcgcctt aggcaaactc cttgacaagg ttcaagccta ctcaactgct      60
ggagggaagg tgtggctgtc agtactttc attttccgaa tcctgctgct ggggacagcg     120
gttgagtcag cctggggaga tgagcagtct gcctttcgtt gtaacactca gcaacctggt     180
tgtgaaaatg tctgctatga caagtctttc ccaatctctc atgtgcgctt ctgggtcctg     240
cagatcatat ttgtgtctgt acccacactc ttgtacctgg ctcatgtgtt ctatgtgatg     300
cgaaaggaag agaaactgaa caagaaagag gaagaactca aggttgccca aactgatggt     360
gtcaatgtgg acatgcactt gaagcagatt gagataaaga agttcaagta cggtattgaa     420
gagcatggta aggtgaaaat gcgaggggggg ttgctgcgaa cctacatcat cagtatcctc     480
ttcaagtcta tctttgaggt ggccttcttg ctgatccagt ggtacatcta tggattcagc     540
ttgagtgctg tttacacttg caaaagagat ccctgcccac atcaggtgga ctgtttcctc     600
tctcgcccca cggagaaaac catcttcatc atcttcatgc tggtggtgtc cttggtgtcc     660
ctggccttga atatcattga actcttctat gttttcttca agggcgttaa ggatcgggtt     720
aagggaaaga gcgacccctta ccatgcgacc agtggtgcgc tgagccctgc caaagactgt     780
gggtctcaaa aatatgctta tttcaatggc tgctcctcac caaccgctcc cctctcgcct     840
atgtctcctc ctgggtacaa gctggttact ggcgacagaa acaattcttc ttgccgcaat     900
tacaacaagc aagcaagtga gcaaaactgg gctaattaca gtgcagaaca aaatcgaatg     960
gggcaggcgg gaagcaccat tctctaactcc catgcacagc cttttgattt ccccgatgat    1020
aaccagaatt ctaaaaaact agctgctgga catgaattac agccactagc cattgtggac    1080
cagcgacctt caagcagagc cagcagtcgt gccagcagca gacctcggcc tgatgacctg    1140
gagatc                                                               1146

<210> SEQ ID NO 3
<211> LENGTH: 281
<212> TYPE: PRT
```

<213> ORGANISM: Homo sapiens

<400> SEQUENCE: 3

Met Arg Lys Glu Glu Lys Leu Asn Lys Lys Glu Glu Leu Lys Val
1               5                   10                  15

Ala Gln Thr Asp Gly Val Asn Val Asp Met His Leu Lys Gln Ile Glu
            20                  25                  30

Ile Lys Lys Phe Lys Tyr Gly Ile Glu Glu His Gly Lys Val Lys Met
            35                  40                  45

Arg Gly Gly Leu Leu Arg Thr Tyr Ile Ile Ser Ile Leu Phe Lys Ser
        50                  55                  60

Ile Phe Glu Val Ala Phe Leu Leu Ile Gln Trp Tyr Ile Tyr Gly Phe
65                  70                  75                  80

Ser Leu Ser Ala Val Tyr Thr Cys Lys Arg Asp Pro Cys Pro His Gln
                85                  90                  95

Val Asp Cys Phe Leu Ser Arg Pro Thr Glu Lys Thr Ile Phe Ile Ile
            100                 105                 110

Phe Met Leu Val Val Ser Leu Val Ser Leu Ala Leu Asn Ile Ile Glu
            115                 120                 125

Leu Phe Tyr Val Phe Phe Lys Gly Val Lys Asp Arg Val Lys Gly Lys
        130                 135                 140

Ser Asp Pro Tyr His Ala Thr Ser Gly Ala Leu Ser Pro Ala Lys Asp
145                 150                 155                 160

Cys Gly Ser Gln Lys Tyr Ala Tyr Phe Asn Gly Cys Ser Ser Pro Thr
                165                 170                 175

Ala Pro Leu Ser Pro Met Ser Pro Pro Gly Tyr Lys Leu Val Thr Gly
            180                 185                 190

Asp Arg Asn Asn Ser Ser Cys Arg Asn Tyr Asn Lys Gln Ala Ser Glu
        195                 200                 205

Gln Asn Trp Ala Asn Tyr Ser Ala Glu Gln Asn Arg Met Gly Gln Ala
    210                 215                 220

Gly Ser Thr Ile Ser Asn Ser His Ala Gln Pro Phe Asp Phe Pro Asp
225                 230                 235                 240

Asp Asn Gln Asn Ser Lys Lys Leu Ala Ala Gly His Glu Leu Gln Pro
                245                 250                 255

Leu Ala Ile Val Asp Gln Arg Pro Ser Ser Arg Ala Ser Ser Arg Ala
            260                 265                 270

Ser Ser Arg Pro Arg Pro Asp Asp Leu
        275                 280

<210> SEQ ID NO 4
<211> LENGTH: 258
<212> TYPE: PRT
<213> ORGANISM: Homo sapiens

<400> SEQUENCE: 4

Met His Leu Lys Gln Ile Glu Ile Lys Lys Phe Lys Tyr Gly Ile Glu
1               5                   10                  15

Glu His Gly Lys Val Lys Met Arg Gly Gly Leu Leu Arg Thr Tyr Ile
            20                  25                  30

Ile Ser Ile Leu Phe Lys Ser Ile Phe Glu Val Ala Phe Leu Leu Ile
            35                  40                  45

Gln Trp Tyr Ile Tyr Gly Phe Ser Leu Ser Ala Val Tyr Thr Cys Lys
        50                  55                  60

Arg Asp Pro Cys Pro His Gln Val Asp Cys Phe Leu Ser Arg Pro Thr

```
            65                  70                  75                  80
    Glu Lys Thr Ile Phe Ile Ile Phe Met Leu Val Val Ser Leu Val Ser
                    85                  90                  95

Leu Ala Leu Asn Ile Ile Glu Leu Phe Tyr Val Phe Lys Gly Val
                    100                 105                 110

Lys Asp Arg Val Lys Gly Lys Ser Asp Pro Tyr His Ala Thr Ser Gly
                    115                 120                 125

Ala Leu Ser Pro Ala Lys Asp Cys Gly Ser Gln Lys Tyr Ala Tyr Phe
                    130                 135                 140

Asn Gly Cys Ser Ser Pro Thr Ala Pro Leu Ser Pro Met Ser Pro Pro
    145                 150                 155                 160

Gly Tyr Lys Leu Val Thr Gly Asp Arg Asn Asn Ser Ser Cys Arg Asn
                    165                 170                 175

Tyr Asn Lys Gln Ala Ser Glu Gln Asn Trp Ala Asn Tyr Ser Ala Glu
                    180                 185                 190

Gln Asn Arg Met Gly Gln Ala Gly Ser Thr Ile Ser Asn Ser His Ala
                    195                 200                 205

Gln Pro Phe Asp Phe Pro Asp Asp Asn Gln Asn Ser Lys Lys Leu Ala
                    210                 215                 220

Ala Gly His Glu Leu Gln Pro Leu Ala Ile Val Asp Gln Arg Pro Ser
    225                 230                 235                 240

Ser Arg Ala Ser Ser Arg Ala Ser Ser Arg Pro Arg Pro Asp Asp Leu
                    245                 250                 255

Glu Ile

<210> SEQ ID NO 5
<211> LENGTH: 236
<212> TYPE: PRT
<213> ORGANISM: Homo sapiens

<400> SEQUENCE: 5

Met Arg Gly Gly Leu Leu Arg Thr Tyr Ile Ile Ser Ile Leu Phe Lys
    1                   5                   10                  15

Ser Ile Phe Glu Val Ala Phe Leu Leu Ile Gln Trp Tyr Ile Tyr Gly
                    20                  25                  30

Phe Ser Leu Ser Ala Val Tyr Thr Cys Lys Arg Asp Pro Cys Pro His
                    35                  40                  45

Gln Val Asp Cys Phe Leu Ser Arg Pro Thr Glu Lys Thr Ile Phe Ile
                    50                  55                  60

Ile Phe Met Leu Val Val Ser Leu Val Ser Leu Ala Leu Asn Ile Ile
    65                  70                  75                  80

Glu Leu Phe Tyr Val Phe Phe Lys Gly Val Lys Asp Arg Val Lys Gly
                    85                  90                  95

Lys Ser Asp Pro Tyr His Ala Thr Ser Gly Ala Leu Ser Pro Ala Lys
                    100                 105                 110

Asp Cys Gly Ser Gln Lys Tyr Ala Tyr Phe Asn Gly Cys Ser Ser Pro
                    115                 120                 125

Thr Ala Pro Leu Ser Pro Met Ser Pro Pro Gly Tyr Lys Leu Val Thr
                    130                 135                 140

Gly Asp Arg Asn Asn Ser Ser Cys Arg Asn Tyr Asn Lys Gln Ala Ser
    145                 150                 155                 160

Glu Gln Asn Trp Ala Asn Tyr Ser Ala Glu Gln Asn Arg Met Gly Gln
                    165                 170                 175

Ala Gly Ser Thr Ile Ser Asn Ser His Ala Gln Pro Phe Asp Phe Pro
```

```
            180                 185                 190
Asp Asp Asn Gln Asn Ser Lys Lys Leu Ala Ala Gly His Glu Leu Gln
                195                 200                 205

Pro Leu Ala Ile Val Asp Gln Arg Pro Ser Ser Arg Ala Ser Ser Arg
        210                 215                 220

Ala Ser Ser Arg Pro Arg Pro Asp Asp Leu Glu Ile
225                 230                 235
```

<210> SEQ ID NO 6
<211> LENGTH: 170
<212> TYPE: PRT
<213> ORGANISM: Homo sapiens

<400> SEQUENCE: 6

```
Met Leu Val Val Ser Leu Val Ser Leu Ala Leu Asn Ile Ile Glu Leu
1               5                   10                  15

Phe Tyr Val Phe Phe Lys Gly Val Lys Asp Arg Val Lys Gly Lys Ser
            20                  25                  30

Asp Pro Tyr His Ala Thr Ser Gly Ala Leu Ser Pro Ala Lys Asp Cys
        35                  40                  45

Gly Ser Gln Lys Tyr Ala Tyr Phe Asn Gly Cys Ser Ser Pro Thr Ala
    50                  55                  60

Pro Leu Ser Pro Met Ser Pro Pro Gly Tyr Lys Leu Val Thr Gly Asp
65                  70                  75                  80

Arg Asn Asn Ser Ser Cys Arg Asn Tyr Asn Lys Gln Ala Ser Glu Gln
                85                  90                  95

Asn Trp Ala Asn Tyr Ser Ala Glu Gln Asn Arg Met Gly Gln Ala Gly
            100                 105                 110

Ser Thr Ile Ser Asn Ser His Ala Gln Pro Phe Asp Phe Pro Asp Asp
        115                 120                 125

Asn Gln Asn Ser Lys Lys Leu Ala Ala Gly His Glu Leu Gln Pro Leu
    130                 135                 140

Ala Ile Val Asp Gln Arg Pro Ser Ser Arg Ala Ser Ser Arg Ala Ser
145                 150                 155                 160

Ser Arg Pro Arg Pro Asp Asp Leu Glu Ile
                165                 170
```

<210> SEQ ID NO 7
<211> LENGTH: 9215
<212> TYPE: DNA
<213> ORGANISM: Artificial Sequence
<220> FEATURE:
<223> OTHER INFORMATION: Adeno cx43 vector

<400> SEQUENCE: 7

```
catcatcaat aatataccct atttggatt gaagccaata tgataatgag ggggtggagt      60
ttgtgacgtg gcgcggggcg tgggaacggg gcgggtgacg tagtagtgtg cggaagtgt     120 gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tactgtaata gtaatcaatt    360
acggggtcat tagttcatag cccatatatg gagttccgcg ttacataact acggtaaat    420 ggcccgcctg gctgaccgcc caacgacccc cgcccattga cgtcaataat gacgtatgtt    480
cccatagtaa cgccaatagg gactttccat tgacgtcaat gggtggagta tttacggtaa    540
```

```
actgcccact tggcagtaca tcaagtgtat catatgccaa gtacgccccc tattgacgtc      600
aatgacggta aatggcccgc ctggcattat gcccagtaca tgaccttatg ggactttcct      660
acttggcagt acatctacgt attagtcatc gctattacca tggtgatgcg gttttggcag      720
tacatcaatg ggcgtggata gcggtttgac tcacggggat ttccaagtct ccaccccatt      780
gacgtcaatg ggagtttgtt ttggcaccaa aatcaacggg actttccaaa atgtcgtaac      840
aactccgccc cattgacgca aatgggcggt aggcgtgtac ggtgggaggt ctatataagc      900
agagctggtt tagtgaaccg tcagatccgc tagattaagt aatacgactc actataggca      960
tggatgggtg actggagcgc cttaggcaaa ctccttgaca aggttcaagc ctactcaact     1020
gctggaggga aggtgtggct gtcagtactt tcattttcc gaatcctgct gctggggaca      1080
gcggttgagt cagcctgggg agatgagcag tctgcctttc gttgtaacac tcagcaacct     1140
ggttgtgaaa atgtctgcta tgacaagtct ttcccaatct ctcatgtgcg cttctgggtc     1200
ctgcagatca tatttgtgtc tgtacccaca ctcttgtacc tggctcatgt gttctatgtg     1260
atgcgaaagg aagagaaact gaacaagaaa gaggaagaac tcaaggttgc ccaaactgat     1320
ggtgtcaatg tggacatgca cttgaagcag attgagataa agaagttcaa gtacggtatt     1380
gaagagcatg gtaaggtgaa aatgcgaggg gggttgctgc gaacctacat catcagtatc     1440
ctcttcaagt ctatctttga ggtggccttc ttgctgatcc agtggtacat ctatggattc     1500
agcttgagtg ctgtttacac ttgcaaaaga gatccctgcc acatcaggt ggactgtttc     1560 ctctctcgcc ccacggagaa aaccatcttc atcatcttca tgctggtggt gtccttggtg     1620
tccctggcct tgaatatcat tgaactcttc tatgttttct tcaagggcgt taaggatcgg     1680
gttaagggaa agagcgaccc ttaccatgcg accagtggtg cgctgagccc tgccaaagac     1740
tgtgggtctc aaaaatatgc ttatttcaat ggctgctcct caccaaccgc tcccctctcg     1800
cctatgtctc ctcctgggta caagctggtt actggcgaca gaaacaattc ttcttgccgc     1860
aattacaaca agcaagcaag tgagcaaaac tgggctaatt acagtgcaga acaaaatcga     1920
atggggcagg cgggaagcac catctctaac tcccatgcac agccttttga ttttccccgat    1980 gatctagcca attcccgtgt gagcaagggc gaggagctgt tcaccggggt ggtgcccatc     2040
ctggtcgagc tggacggcga cgtaaacggc cacaagttca gcgtgtccgg cgagggcgag     2100
ggcgatgcca cctacggcaa gctgaccctg aagttcatct gcaccaccgg caagctgccc     2160 gtgcccctggc ccaccctcgt gaccaccttc ggctacggcg tgcagtgctt cgcccgctac     2220
cccgaccaca tgaagcagca cgacttcttc aagtccgcca tgcccgaagg ctacgtccag     2280
gagcgcacca tcttcttcaa ggacgacggc aactacaaga cccgcgccga ggtgaagttc     2340
gagggcgaca cccctggtgaa ccgcatcgag ctgaagggca tcgacttcaa ggaggacggc     2400
aacatcctgg ggcacaagct ggagtacaac tacaacagcc acaacgtcta tatcatggcc     2460
gacaagcaga agaacggcat caaggtgaac ttcaagatcc gccacaacat cgaggacggc     2520
agcgtgcagc tcgccgacca ctaccagcag aacacccca tcggcgacgg ccccgtgctg     2580
ctgcccgaca ccactaccct gagctaccag tccgccctga gcaaagaccc caacgagaag     2640
cgcgatcaca tggtcctgct ggagttcgtg accgccgccg ggatcactct cggcatggac     2700
gagctgtaca agtaagcttc tagataagat atccgatcca ccggatctag ataactgatc     2760
ataatcagcc ataccacatt tgtagaggtt ttacttgctt taaaaaacct cccacacctc     2820
cccctgaacc tgaaacataa aatgaatgca attgttgttg ttaacttgtt tattgcagct    2880
```

-continued

```
tataatggtt acaaataaag caatagcatc acaaatttca caaataaagc attttttttca    2940
ctgcattcta gttgtggttt gtccaaactc atcaatgtat cttaacgcgg atctgggcgt    3000
ggttaagggt gggaaagaat atataaggtg ggggtcttat gtagttttgt atctgttttg    3060
cagcagccgc cgccgccatg agcaccaact cgtttgatgg aagcattgtg agctcatatt    3120
tgacaacgcg catgccccca tgggccgggg tgcgtcagaa tgtgatgggc tccagcattg    3180
atggtcgccc cgtcctgccc gcaaactcta ctaccttgac ctacgagacc gtgtctggaa    3240
cgccgttgga gactgcagcc tccgccgccg cttcagccgc tgcagccacc gcccgcggga    3300
ttgtgactga ctttgctttc ctgagccgc ttgcaagcag tgcagcttcc cgttcatccg    3360
cccgcgatga caagttgacg gctctttttgg cacaattgga ttctttgacc cgggaactta    3420
atgtcgtttc tcagcagctg ttggatctgc ccagcaggt ttctgccctg aaggcttcct    3480
cccctcccaa tgcggtttaa acataaata aaaaaccaga ctctgtttgg atttggatca    3540
agcaagtgtc ttgctgtctt tatttagggg ttttgcgcgc gcggtaggcc cgggaccagc    3600
ggtctcggtc gttgagggtc ctgtgtattt ttttccaggac gtggtaaagg tgactctgga    3660
tgttcagata catgggcata agcccgtctc tggggtggag gtagcaccac tgcagagctt    3720
catgctgcgg ggtggtgttg tagatgatcc agtcgtagca ggagcgctgg gcgtggtgcc    3780
taaaaatgtc tttcagtagc aagctgattg ccaggggcag gcccttggtg taagtgttta    3840
caaagcggtt aagctgggat gggtgcatac gtggggatat gagatgcatc ttggactgta    3900
tttttaggtt ggctatgttc ccagccatat ccctccgggg attcatgttg tgcagaacca    3960
ccagcacagt gtatccggtg cacttgggaa atttgtcatg tagcttagaa ggaaatgcgt    4020
ggaagaactt ggagacgccc ttgtgacctc caagattttc catgcattcg tccataatga    4080
tggcaatggg cccacgggcg gcggcctggg cgaagatatt tctgggatca ctaacgtcat    4140
agttgtgttc caggatgaga tcgtcatagg ccatttttac aaagcgcggg cggagggtgc    4200
cagactgcgg tataatggtt ccatccggcc caggggcgta gttaccctca cagatttgca    4260
tttcccacgc tttgagttca gatgggggga tcatgtctac ctgcggggcg atgaagaaaa    4320
cggtttccgg ggtagggggag atcagctggg aagaaagcag gttcctgagc agctgcgact    4380
taccgcagcc ggtgggcccg taaatcacac ctattaccgg ctgcaactgg tagttaagag    4440
agctgcagct gccgtcatcc ctgagcaggg gggccacttc gttaagcatg tccctgactc    4500
gcatgttttc cctgaccaaa tccgccagaa ggcgctcgcc gcccagcgat agcagttctt    4560
gcaaggaagc aaagtttttc aacggtttga gaccgtccgc cgtaggcatg cttttgagcg    4620
tttgaccaag cagttccagg cggtcccaca gctcggtcac ctgctctacg gcatctcgat    4680
ccagcatatc tcctcgtttc gcggttggg gcggcttttcg ctgtacggca gtagtcggtg    4740
ctcgtccaga cgggccaggg tcatgtcttt ccacgggcgc agggtcctcg tcagcgtagt    4800
ctgggtcacg gtgaagggggt gcgctccggg ctgcgcgctg ccagggtgc gcttgaggct    4860
ggtcctgctg gtgctgaagc gctgccggtc ttcgccctgc gcgtcggcca ggtagcattt    4920
gaccatggtg tcatagtcca gcccctccgc ggcgtggccc ttggcgcgca gcttgccctt    4980
ggaggaggcg ccgcacgagg ggcagtgcag acttttgagg gcgtagagct tgggcgcgag    5040
aaataccgat tccggggagt aggcatccgc gccgcaggcc ccgcagacgg tctcgcattc    5100
cacgagccag gtgagctctg gccgttcggg gtcaaaaacc aggtttcccc catgcttttt    5160
gatgcgtttt ttacctctgg tttccatgag ccggtgtcca cgctcggtga cgaaaaggct    5220
gtccgtgtcc ccgtatacag acttgagagg gagtttaaac gaattcaata gcttgttgca    5280
```

```
tgggcggcga tataaaatgc aaggtgctgc tcaaaaaatc aggcaaagcc tcgcgcaaaa    5340
aagaaagcac atcgtagtca tgctcatgca gataaaggca ggtaagctcc ggaaccacca    5400
cagaaaaaga caccattttt ctctcaaaca tgtctgcggg tttctgcata aacacaaaat    5460
aaaataacaa aaaacatttt aaacattaga agcctgtctt acaacaggaa aaacaaccct    5520
tataagcata agacggacta cggccatgcc ggcgtgaccg taaaaaaact ggtcaccgtg    5580
attaaaaagc accaccgaca gctcctcggt catgtccgga gtcataatgt aagactcggt    5640
aaacacatca ggttgattca catcggtcag tgctaaaaag cgaccgaaat agcccggggg    5700
aatacatacc cgcaggcgta gagacaacat tacagccccc ataggaggta taacaaaatt    5760
aataggagag aaaaacacat aaacacctga aaaaccctcc tgcctaggca aaatagcacc    5820
ctcccgctcc agaacaacat acagcgcttc cacagcggca gccataacag tcagccttac    5880
cagtaaaaaa gaaaacctat taaaaaaaca ccactcgaca cggcaccagc tcaatcagtc    5940
acagtgtaaa aaagggccaa gtgcagagcg agtatatata ggactaaaaa atgacgtaac    6000
ggttaaagtc cacaaaaaac acccagaaaa ccgcacgcga acctacgccc agaaacgaaa    6060
gccaaaaaac ccacaacttc ctcaaatcgt cacttccgtt ttcccacgtt acgtcacttc    6120
ccattttaag aaaactacaa ttcccaacac atacaagtta ctccgcccta aaacctacgt    6180
cacccgcccc gttcccacgc cccgcgccac gtcacaaact ccaccccctc attatcatat    6240
tggcttcaat ccaaaataag gtatattatt gatgatgtta attaacatgc atggatccat    6300
atgcggtgtg aaataccgca cagatgcgta aggagaaaat accgcatcag gcgctcttcc    6360
gcttcctcgc tcactgactc gctgcgctcg tcgttcggc tgcggcgagc ggtatcagct    6420
cactcaaagg cggtaatacg gttatccaca gaatcagggg ataacgcagg aaagaacatg    6480
tgagcaaaag gccagcaaaa ggccaggaac cgtaaaaagg ccgcgttgct ggcgtttttc    6540
cataggctcc gcccccctga cgagcatcac aaaaatcgac gctcaagtca gaggtggcga    6600
aacccgacag gactataaag ataccaggcg tttccccctg gaagctccct cgtgcgctct    6660
cctgttccga ccctgccgct taccggatac ctgtccgcct ttctcccttc gggaagcgtg    6720
gcgctttctc atagctcacg ctgtaggtat ctcagttcgg tgtaggtcgt tcgctccaag    6780
ctgggctgtg tgcacgaacc ccccgttcag cccgaccgct gcgccttatc cggtaactat    6840
cgtcttgagt ccaacccggt aagacacgac ttatcgccac tggcagcagc cactggtaac    6900
aggattagca gagcgaggta tgtaggcggt gctacagagt tcttgaagtg gtggcctaac    6960
tacggctaca ctagaaggac agtatttggt atctgcgctc tgctgaagcc agttaccttc    7020
ggaaaaagag ttggtagctc ttgatccggc aaacaaacca ccgctggtag cggtggtttt    7080
tttgtttgca agcagcagat tacgcgcaga aaaaaggat ctcaagaaga tcctttgatc    7140
ttttctacgg ggtctgacgc tcagtggaac gaaaactcac gttaagggat tttggtcatg    7200
agattatcaa aaaggatctt cacctagatc cttttaaatt aaaaatgaag ttttaaatca    7260
atctaaagta tatatgagta aacttggtct gacagttacc aatgcttaat cagtgaggca    7320
cctatctcag cgatctgtct atttcgttca tccatagttg cctgactccc cgtcgtgtag    7380
ataactacga tacgggaggg cttaccatct ggccccagtg ctgcaatgat accgcgagac    7440
ccacgctcac cggctccaga tttatcagca ataaaccagc cagccggaag ggccgagcgc    7500
agaagtggtc ctgcaacttt atccgcctcc atccagtcta ttaattgttg ccgggaagct    7560
agagtaagta gttcgccagt taatagtttg cgcaacgttg ttgccattgc tgcagccatg    7620
```

| | |
|---|---:|
| agattatcaa aaaggatctt cacctagatc cttttcacgt agaaagccag tccgcagaaa | 7680 |
| cggtgctgac cccggatgaa tgtcagctac tgggctatct ggacaaggga aaacgcaagc | 7740 |
| gcaaagagaa agcaggtagc ttgcagtggg cttacatggc gatagctaga ctgggcggtt | 7800 |
| ttatggacag caagcgaacc ggaattgcca gctgggcgc cctctggtaa ggttgggaag | 7860 |
| ccctgcaaag taaactggat ggcttcttg ccgccaagga tctgatggcg cagggatca | 7920 |
| agctctgatc aagagacagg atgaggatcg tttcgcatga ttgaacaaga tggattgcac | 7980 |
| gcaggttctc cggccgcttg ggtggagagg ctattcggct atgactgggc acaacagaca | 8040 |
| atcggctgct ctgatgccgc cgtgttccgg ctgtcagcgc agggcgccc ggttcttttt | 8100 |
| gtcaagaccg acctgtccgg tgccctgaat gaactgcaag acgaggcagc gcggctatcg | 8160 |
| tggctggcca cgacgggcgt tccttgcgca gctgtgctcg acgttgtcac tgaagcggga | 8220 |
| agggactggc tgctattggg cgaagtgccg gggcaggatc tcctgtcatc tcaccttgct | 8280 |
| cctgccgaga agtatccat catggctgat gcaatgcggc ggctgcatac gcttgatccg | 8340 |
| gctacctgcc cattcgacca ccaagcgaaa catcgcatcg agcgagcacg tactcggatg | 8400 |
| gaagccggtc ttgtcgatca ggatgatctg gacgaagagc atcaggggct cgcgccagcc | 8460 |
| gaactgttcg ccaggctcaa ggcgagcatg cccgacggcg aggatctcgt cgtgacccat | 8520 |
| ggcgatgcct gcttgccgaa tatcatggtg gaaaatggcc gcttttctgg attcatcgac | 8580 |
| tgtggccggc tgggtgtggc ggaccgctat caggacatag cgttggctac ccgtgatatt | 8640 |
| gctgaagagc ttggcggcga atgggctgac cgcttcctcg tgctttacgg tatcgccgct | 8700 |
| cccgattcgc agcgcatcgc cttctatcgc cttcttgacg agttcttctg aattttgtta | 8760 |
| aaattttgt taaatcagct cattttttaa ccataggcc gaaatcggca ccatcccta | 8820 |
| taaatcaaaa gaatagaccg agatagggtt gagtgttgtt ccagtttgga acaagagtcc | 8880 |
| actattaaag aacgtggact ccaacgtcaa agggcgaaaa accgtctatc agggcgatgg | 8940 |
| cccactacgt gaaccatcac cctaatcaag ttttttgtgg tcgaggtgcc gtaaagcact | 9000 |
| aaatcggaac cctaaaggga gcccccgatt tagagcttga cggggaaagc cggcgaacgt | 9060 |
| ggcgagaaag gaagggaaga agcgaaagg agcgggcgct agggcgctgg caagtgtagc | 9120 |
| ggtcacgctg cgcgtaacca ccacacccgc gcgcttaatg cgccgctaca gggcgcgtcc | 9180 |
| attcgccatt caggatcgaa ttaattctta attaa | 9215 |

<210> SEQ ID NO 8
<211> LENGTH: 6146
<212> TYPE: DNA
<213> ORGANISM: Artificial Sequence
<220> FEATURE:
<223> OTHER INFORMATION: pAAV-tnt-GFP-CX43 vector sequence

<400> SEQUENCE: 8

| | |
|---|---:|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctaccag ggtaatgggg | 180 |
| atcctctaga actatagcta gaattcgccc ttacgggccc ccctcgagg tcgggataaa | 240 |
| agcagtctgg gctttcacat gacagcatct ggggctgcgg cagagggtcg ggtccgaagc | 300 |
| gctgccttat cagcgtcccc agccctggga ggtgacagct ggctggcttg tgtcagcccc | 360 |
| tcgggcactc acgtatctcc gtccgacggg tttaaaatag caaaactctg aggccacaca | 420 |
| atagcttggg cttatatggg ctcctgtggg ggaagggga gcacggaggg ggccggggcc | 480 |

```
gctgctgcca aaatagcagc tcacaagtgt tgcattcctc tctgggcgcc gggcacattc    540
ctgctggctc tgcccgcccc ggggtgggcg ccggggggac cttaaagcct ctgcccccca    600
aggagccctt cccagacagc cgccggcacc caccgctccg tgggacgatc cccgaagctc    660
tagagcttta ttgcggtagt ttatcacagt taaattgcta acgcagtcag tgcttctgac    720
acaacagtgg tcgtgaggca ctgggcaggt aagtatcaag gttacaagac aggtttaagg    780
agaccaatag aaactgggct tgtcgagaca gagaagactc ttgcgtttct gataggcacc    840
tattggtctt actgacatcc actttgcctt tctctccaca ggtgtccact cccagttcaa    900
ttacagctct taaggctaga gtacttaata cgactcacta taggctagcg ctaccggtcg    960
ccaccatggt gagcaagggc gccgagctgt tcaccggcat cgtgcccatc ctgatcgagc   1020
tgaatggcga tgtgaatggc cacaagttca gcgtgagcgg cgagggcgag ggcgatgcca   1080
cctacggcaa gctgaccctg aagttcatct gcaccaccgg caagctgcct gtgccctggc   1140
ccacccctgt gaccaccctg agctacggcg tgcagtgctt ctcacgctac ccgatcaca   1200 tgaagcagca cgacttcttc aagagcgcca tgcctgaggg ctacatccag agcgcacca   1260 tcttcttcga ggatgacggc aactacaagt cgcgcgccga ggtgaagttc gagggcgata   1320
ccctggtgaa tcgcatcgag ctgaccggca ccgatttcaa ggaggatggc aacatcctgg   1380
gcaataagat ggagtacaac tacaacgccc acaatgtgta catcatgacc gacaaggcca   1440
agaatggcat caaggtgaac ttcaagatcc gccacaacat cgaggatggc agcgtgcagc   1500
tggccgacca ctaccagcag aatacccca tcggcgatgg ccctgtgctg ctgcccgata   1560
accactacct gtccacccag agcgccctgt ccaaggaccc caacgagaag cgcgatcaca   1620
tgatctactt cggcttcgtg accgccgccg ccatcaccca cggcatggat gagctgtaca   1680
agtccggact cagatctcga gctcaagctt cgaattctgc agtcgacggt accgagctcg   1740
gatccactag taacggccgc cagtgtgctg gaattcggct tatgggtgac tggagcgcct   1800
taggcaaact ccttgacaag gttcaagcct actcaactgc tggagggaag gtgtggctgt   1860
cagtactttt cattttccga atcctgctgc tgggacagc ggttgagtca gcctggggag   1920
atgagcagtc tgcctttcgt tgtaacactc agcaacctgg ttgtgaaaat gtctgctatg   1980
acaagtcttt cccaatctct catgtgcgct tctgggtcct gcagatcata tttgtgtctg   2040
tacccacact cttgtacctg gctcatgtgt tctatgtgat gcgaaggaa gagaaactga   2100 acaagaaaga ggaagaactc aaggttgccc aaactgatgg tgtcaatgtg gacatgcact   2160
tgaagcagat tgagataaag aagttcaagt acggtattga agagcatggt aaggtgaaaa   2220
tgcgaggggg gttgctgcga acctacatca tcagtatcct cttcaagtct atctttgagg   2280
tggccttctt gctgatccag tggtacatct atggattcag cttgagtgct gtttacactt   2340
gcaaaagaga tccctgccca catcaggtgg actgtttcct ctctcgcccc acggagaaaa   2400
ccatcttcat catcttcatg ctggtggtgt ccttggtgtc cctggccttg aatatcattg   2460
aactcttcta tgttttcttc aagggcgtta aggatcgggt taagggaaag agcgacccgtt   2520 accatgcgac cagtggtgcg ctgagccctg ccaaagactg tgggtctcaa aaatatgctt   2580
atttcaatgg ctgctcctca ccaaccgctc ccctctcgcc tatgtctcct cctgggtaca   2640
agctggttac tggcgacaga aacaattctt cttgccgcaa ttacaacaag caagcaagtg   2700
agcaaaactg ggctaattac agtgcagaac aaaatcgaat ggggcaggcg ggaagcacca   2760
tctctaactc ccatgcacag ccttttgatt tccccgatga taaccagaat tcaaaaaaac   2820
```

```
tagctgctgg acatgaatta cagccactag ccattgtgga ccagcgacct tcaagcagag   2880
ccagcagtcg tgccagcagc agacctcggc ctgatgacct ggagatctaa tctaggaccc   2940
gggcggcctc gaggacgggg tgaactacgc ctgaggatcc gatctttttc cctctgccaa   3000
aaattatggg gacatcatga agcccttga gcatctgact tctggctaat aaaggaaatt    3060 tatttcatt gcaatagtgt gttggaattt tttgtgtctc tcactcggaa gcaattcgtt    3120
gatctgaatt tcgaccaccc ataatacca ttacctggt agataagtag catgcgggt     3180 taatcattaa ctacaaggaa ccctagtga tggagttggc cactccctct ctgcgcgctc    3240
gctcgctcac tgaggccggg cgaccaaagg tcgcccgacg cccgggcttt gcccgggcgg   3300
cctcagtgag cgagcgagcg cgcagcctta attaacctaa ttcactggcc gtcgttttac   3360
aacgtcgtga ctgggaaaac cctggcgtta cccaacttaa tcgccttgca gcacatcccc   3420
ctttcgccag ctggcgtaat agcgaagagg cccgcaccga tcgcccttcc caacagttgc   3480
gcagcctgaa tggcgaatgg gacgcgccct gtagcggcgc attaagcgcg gcgggtgtgg   3540
tggttacgcg cagcgtgacc gctacacttg ccagcgccct agcgcccgct cctttcgctt   3600 tcttccctttc ctttctcgcc acgttcgccg gctttccccg tcaagctcta atcggggc    3660 tcccttagg gttccgattt agtgctttac ggcacctcga ccccaaaaaa cttgattagg   3720
gtgatggttc acgtagtggg ccatcgccct gatagacggt ttttcgccct ttgacgttgg   3780
agtccacgtt ctttaatagt ggactcttgt tccaaactgg aacaacactc aaccctatct   3840
cggtctattc ttttgattta aagggattt tgccgatttc ggcctattgg ttaaaaaatg   3900
agctgattta acaaaaattt aacgcgaatt ttaacaaaat attaacgctt acaattttagg   3960 tggcactttt cggggaaatg tgcgcggaac ccctatttgt ttattttctct aaatacattc   4020 aaatatgtat ccgctcatga caataaccc tgataaatg cttcaataat attgaaaaag    4080
gaagagtatg agtattcaac atttccgtgt cgcccttatt ccctttttg cggcattttg    4140 ccttcctgtt tttgctcacc cagaaacgct ggtgaaagta aaagatgctg aagatcagtt   4200
gggtgcacga gtgggttaca tcgaactgga tctcaacagc ggtaagatcc ttgagagtttt   4260 tcgccccgaa gaacgttttc caatgatgag cacttttaaa gttctgctat gtggcgcggt   4320
attatcccgt attgacgccg ggcaagagca actcggtcgc cgcatacact attctcagaa   4380
tgacttggtt gagtactcac cagtcacaga aaagcatctt acggatggca tgacagtaag   4440
agaattatgc agtgctgcca taaccatgag tgataacact gcggccaact tacttctgac   4500
aacgatcgga ggaccgaagg agctaaccgc ttttttgcac aacatggggg atcatgtaac   4560
tcgccttgat cgttgggaac cggagctgaa tgaagccata ccaaacgacg agcgtgacac   4620
cacgatgcct gtagcaatgg caacaacgtt gcgcaaacta ttaactgcg aactacttac    4680 tctagcttcc cggcaacaat aatagactg gatggaggcg gataaagttg caggaccact    4740
tctgcgctcg gcccttccgg ctggctggtt tattgctgat aaatctggag ccggtgagcg   4800
tgggtctcgc ggtatcattg cagcactggg gccagatggt aagccctccc gtatcgtagt   4860
tatctacacg acggggagtc aggcaactat ggatgaacga atagacaga tcgctgagat    4920 aggtgcctca ctgattaagc attggtaact gtcagaccaa gtttactcat atatacttta    4980
gattgattta aaacttcatt tttaattaa aaggatctag gtgaagatcc tttttgataa    5040
tctcatgacc aaaatccctt aacgtgagtt ttcgttccac tgagcgtcag accccgtaga   5100
aaagatcaaa ggatcttctt gagatccttt ttttctgcgc gtaatctgct gcttgcaaac   5160
aaaaaaacca ccgctaccag cggtggtttg tttgccggat caagagctac caactctttt   5220
```

```
tccgaaggta actggcttca gcagagcgca gataccaaat actgttcttc tagtgtagcc    5280
gtagttaggc caccacttca agaactctgt agcaccgcct acatacctcg ctctgctaat    5340
cctgttacca gtggctgctg ccagtggcga taagtcgtgt cttaccgggt tggactcaag    5400
acgatagtta ccggataagg cgcagcggtc gggctgaacg gggggttcgt gcacacagcc    5460
cagcttggag cgaacgacct acaccgaact gagataccta cagcgtgagc tatgagaaag    5520
cgccacgctt cccgaaggga gaaaggcgga caggtatccg gtaagcggca gggtcggaac    5580
aggagagcgc acgagggagc ttccaggggg aaacgcctgg tatctttata gtcctgtcgg    5640
gtttcgccac ctctgacttg agcgtcgatt tttgtgatgc tcgtcagggg ggcggagcct    5700
atggaaaaac gccagcaacg cggccttttt acggttcctg gccttttgct ggccttttgc    5760
tcacatgttc tttcctgcgt tatcccctga ttctgtggat aaccgtatta ccgcctttga    5820
gtgagctgat accgctcgcc gcagccgaac gaccgagcgc agcgagtcag tgagcgagga    5880
agcggaagag cgcccaatac gcaaaccgcc tctccccgcg cgttggccga ttcattaatg    5940
cagctggcac gacaggtttc ccgactggaa agcgggcagt gagcgcaacg caattaatgt    6000
gagttagctc actcattagg caccccaggc tttacacttt atgcttccgg ctcgtatgtt    6060
gtgtggaatt gtgagcggat aacaatttca cacaggaaac agctatgacc atgattacgc    6120
cagatttaat taaggcctta attagg                                         6146
```

<210> SEQ ID NO 9
<211> LENGTH: 849
<212> TYPE: DNA
<213> ORGANISM: Homo sapiens

<400> SEQUENCE: 9

```
atgcgaaagg aagagaaact gaacaagaaa gaggaagaac tcaaggttgc ccaaactgat     60
ggtgtcaatg tggacatgca cttgaagcag attgagataa agaagttcaa gtacggtatt    120
gaagagcatg gtaaggtgaa aatgcgaggg gggttgctgc gaacctacat catcagtatc    180
ctcttcaagt ctatctttga ggtggccttc ttgctgatcc agtggacat ctatggattc    240 agcttgagtg ctgtttacac ttgcaaaaga gatccctgcc acatcaggt ggactgtttc    300 ctctctcgcc ccacggagaa aaccatcttc atcatcttca tgctggtggt gtccttggtg    360
tccctggcct tgaatatcat tgaactcttc tatgttttct tcaagggcgt taaggatcgg    420
gttaagggaa agagcgaccc ttaccatgcg accagtggtg cgctgagccc tgccaaagac    480
tgtgggtctc aaaaatatgc ttatttcaat ggctgctcct caccaaccgc tcccctctcg    540
cctatgtctc ctcctgggta caagctggtt actggcgaca gaaacaattc ttcttgccgc    600
aattacaaca gcaagcaag tgagcaaaac tgggctaatt acagtgcaga acaaaatcga    660
atggggcagg cgggaagcac catctctaac tcccatgcac agccttttga tttccccgat    720
gataaccaga attctaaaaa actagctgct ggacatgaat acagccact agccattgtg    780 gaccagcgac cttcaagcag agccagcagt cgtgccagca gcagacctcg gcctgatgac    840
ctggagatc                                                            849
```

<210> SEQ ID NO 10
<211> LENGTH: 774
<212> TYPE: DNA
<213> ORGANISM: Homo sapiens

<400> SEQUENCE: 10

```
atgcacttga agcagattga gataaagaag ttcaagtacg gtattgaaga gcatggtaag    60
gtgaaaatgc gagggggtt gctgcgaacc tacatcatca gtatcctctt caagtctatc    120
tttgaggtgg ccttcttgct gatccagtgg tacatctatg gattcagctt gagtgctgtt    180
tacacttgca aaagagatcc ctgcccacat caggtggact gtttcctctc tcgcccacg    240 gagaaaacca tcttcatcat cttcatgctg gtggtgtcct tggtgtccct ggccttgaat    300
atcattgaac tcttctatgt tttcttcaag ggcgttaagg atcgggttaa gggaaagagc    360
gacccttacc atgcgaccag tggtgcgctg agccctgcca aagactgtgg gtctcaaaaa    420
tatgcttatt tcaatggctg ctcctcacca accgctcccc tctcgcctat gtctcctcct    480
gggtacaagc tggttactgg cgacagaaac aattcttctt gccgcaatta caacaagcaa    540
gcaagtgagc aaaactgggc taattacagt gcagaacaaa atcgaatggg gcaggcggga    600
agcaccatct ctaactccca tgcacagcct tttgatttcc ccgatgataa ccagaattct    660
aaaaaactag ctgctggaca tgaattacag ccactagcca ttgtggacca gcgaccttca    720
agcagagcca gcagtcgtgc cagcagcaga cctcggcctg atgacctgga gatc          774
```

```
<210> SEQ ID NO 11
<211> LENGTH: 708
<212> TYPE: DNA
<213> ORGANISM: Homo sapiens

<400> SEQUENCE: 11
```

```
atgcgagggg ggttgctgcg aacctacatc atcagtatcc tcttcaagtc tatctttgag    60
gtggccttct gctgatcca gtggtacatc tatggattca gcttgagtgc tgtttacact    120
tgcaaaagag atccctgccc acatcaggtg gactgtttcc tctctcgccc cacggagaaa    180
accatcttca tcatcttcat gctggtggtg tccttggtgt ccctggcctt gaatatcatt    240
gaactcttct atgttttctt caagggcgtt aaggatcggg ttaagggaaa gagcgaccct    300
taccatgcga ccagtggtgc gctgagccct gccaaagact gtgggtctca aaaatatgct    360
tatttcaatg gctgctcctc accaaccgct cccctctcgc ctatgtctcc tcctgggtac    420
aagctggtta ctggcgacag aaacaattct tcttgccgca attacaacaa gcaagcaagt    480
gagcaaaact gggctaatta cagtgcagaa caaaatcgaa tggggcaggc gggaagcacc    540
atctctaact cccatgcaca gccttttgat ttccccgatg ataaccagaa ttctaaaaaa    600
ctagctgctg gacatgaatt acagccacta gccattgtgg accagcgacc ttcaagcaga    660
gccagcagtc gtgccagcag cagacctcgg cctgatgacc tggagatc                 708
```

```
<210> SEQ ID NO 12
<211> LENGTH: 510
<212> TYPE: DNA
<213> ORGANISM: Homo sapiens

<400> SEQUENCE: 12
```

```
atgctggtgg tgtccttggt gtccctggcc ttgaatatca ttgaactctt ctatgttttc    60
ttcaagggcg ttaaggatcg ggttaaggga agagcgacc cttaccatgc gaccagtggt    120
gcgctgagcc ctgccaaaga ctgtgggtct caaaaatatg cttatttcaa tggctgctcc    180
tcaccaaccg ctcccctctc gcctatgtct cctcctgggt acaagctggt tactggcgac    240
agaaacaatt cttcttgccg caattacaac aagcaagcaa gtgagcaaaa ctgggctaat    300
tacagtgcag aacaaaatcg aatggggcag gcgggaagca ccatctctaa ctcccatgca    360
cagccttttg atttccccga tgataaccag aattctaaaa aactagctgc tggacatgaa    420
```

```
ttacagccac tagccattgt ggaccagcga ccttcaagca gagccagcag tcgtgccagc    480
agcagacctc ggcctgatga cctggagatc                                    510
```